(12) United States Patent
Kawabe et al.

(10) Patent No.: US 10,797,248 B2
(45) Date of Patent: Oct. 6, 2020

(54) ORGANIC ELECTROLUMINESCENT ELEMENT, LIGHTING DEVICE, AND DISPLAY DEVICE

(71) Applicant: Konica Minolta, Inc., Tokyo (JP)

(72) Inventors: Satomi Kawabe, Hachioji (JP); Motoaki Sugino, Akishima (JP); Shinya Otsu, Musashino (JP)

(73) Assignee: KONICA MINOLTA, INC., Tokyo (JP)

(*) Notice: Subject to any disclaimer, the term of this patent is extended or adjusted under 35 U.S.C. 154(b) by 45 days.

(21) Appl. No.: 15/102,613

(22) PCT Filed: Dec. 2, 2014

(86) PCT No.: PCT/JP2014/081827
§ 371 (c)(1),
(2) Date: Jun. 8, 2016

(87) PCT Pub. No.: WO2015/087739
PCT Pub. Date: Jun. 18, 2015

(65) Prior Publication Data
US 2016/0315273 A1 Oct. 27, 2016

(30) Foreign Application Priority Data

Dec. 9, 2013 (JP) ................................ 2013-253754

(51) Int. Cl.
*H01L 51/00* (2006.01)
*C09K 11/06* (2006.01)
(Continued)

(52) U.S. Cl.
CPC .......... *H01L 51/0085* (2013.01); *C07C 49/92* (2013.01); *C07F 15/0033* (2013.01);
(Continued)

(58) Field of Classification Search
CPC ...... H01L 51/0085–0088; C07F 15/0033–004; C07F 15/0086–0093; C09K 2211/185
See application file for complete search history.

(56) References Cited

U.S. PATENT DOCUMENTS 6,936,716 B1 * 8/2005 Lin ..................... C07F 15/0033
428/432
9,748,501 B2 * 8/2017 Otsu ..................... H05B 33/14
(Continued)

FOREIGN PATENT DOCUMENTS

CA 2809518 A1 * 9/2014 .......... C07F 15/0086
JP 2008013616 A * 1/2008
(Continued)

OTHER PUBLICATIONS

Machine Translation of WO-2008140069-A1.*
(Continued)

*Primary Examiner* — William E McClain
(74) *Attorney, Agent, or Firm* — Lucas & Mercanti, LLP

(57) ABSTRACT

An object of the present invention is to provide an organic EL element which has a shorter maximum luminescent wavelength, a long luminous lifespan, a low driving voltage, a small time-dependent change in driving voltage, and a small change in external extraction quantum efficiency even when being used at a high temperature. In addition, an object of the present invention is to provide a lighting device and a display device including the organic EL element.
(Continued)

The organic EL element of the present invention is an organic EL element including: at least one luminous layer sandwiched between a positive electrode and a negative electrode, wherein the luminous layer contains at least one kind of phosphorescent organometallic complex having a structure represented by the following Formula (1):

[Chemical Formula 1]

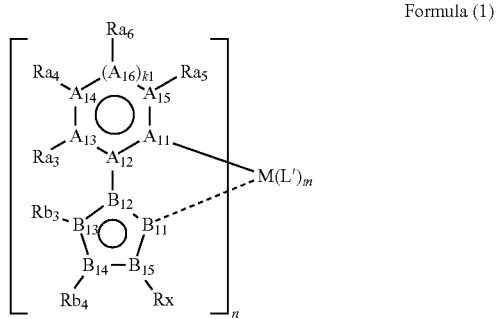

Formula (1)

7 Claims, 5 Drawing Sheets

(51) Int. Cl.
    C07C 49/92      (2006.01)
    C07F 15/00      (2006.01)
    H01L 51/50      (2006.01)
(52) U.S. Cl.
    CPC .......... *C07F 15/0086* (2013.01); *C09K 11/06* (2013.01); *H01L 51/0087* (2013.01); *H01L 51/0094* (2013.01); *C09K 2211/1007* (2013.01); *C09K 2211/1011* (2013.01); *C09K 2211/1014* (2013.01); *C09K 2211/1029* (2013.01); *C09K 2211/1033* (2013.01); *C09K 2211/1044* (2013.01); *C09K 2211/1059* (2013.01); *C09K 2211/1088* (2013.01); *C09K 2211/1092* (2013.01); *C09K 2211/185* (2013.01); *H01L 51/0072* (2013.01); *H01L 51/0073* (2013.01); *H01L 51/0081* (2013.01); *H01L 51/5016* (2013.01)

(56) References Cited

U.S. PATENT DOCUMENTS

| | | | | |
|---|---|---|---|---|
| 2006/0008670 A1* | 1/2006 | Lin | ........................ | C07D 231/12 428/690 |
| 2007/0009759 A1* | 1/2007 | Burn | .................... | C07F 15/0033 428/690 |
| 2007/0196690 A1* | 8/2007 | Ikemizu | .............. | C07F 15/0033 428/690 |
| 2010/0244007 A1* | 9/2010 | Ono | ........................ | C09K 11/06 257/40 |
| 2013/0328037 A1* | 12/2013 | Oshiyama | ........... | H01L 51/0084 257/40 |
| 2014/0124760 A1* | 5/2014 | Das | ..................... | H01L 51/0085 257/40 |
| 2014/0158998 A1* | 6/2014 | Noh | ..................... | H01L 51/0085 257/40 |

FOREIGN PATENT DOCUMENTS

| | | | | | |
|---|---|---|---|---|---|
| JP | WO-2008140069 A1 | * | 11/2008 | .......... | C07F 15/0033 |
| JP | WO-2008143059 A1 | * | 11/2008 | .......... | C07F 15/0033 |
| JP | 2009096861 A | * | 5/2009 | | |
| JP | 2009096861 A | | 5/2009 | | |
| JP | 2010120893 A | * | 6/2010 | | |
| JP | 2010215759 A | | 9/2010 | | |
| JP | 2011205138 A | | 10/2011 | | |
| JP | 2012164731 A | | 8/2012 | | |
| JP | WO-2012111548 A1 | * | 8/2012 | .......... | H01L 51/0085 |
| JP | 2013149880 A | * | 8/2013 | | |
| JP | 2013191804 A | | 9/2013 | | |
| WO | 2007029461 A1 | | 3/2007 | | |
| WO | 2007029533 A1 | | 3/2007 | | |
| WO | 2010016990 A1 | | 2/2010 | | |
| WO | WO-2012111548 A1 | * | 8/2012 | .......... | H01L 51/0085 |
| WO | WO-2014023377 A2 | * | 2/2014 | .......... | C07F 15/0033 |

OTHER PUBLICATIONS

Machine translation of JP-2013149880-A.*
Machine translation of JP-2008013616-A.*
Seo, et al. "Blue organic light-emitting diodes with efficient host-dopant energy level alignment." Current Applied Physics 11.3 (2011): S356-S358.*
Machine translation of WO 2007/029461 A1.*
Wang, et al. "Shedding light on the photophysical properties of iridium (III) complexes with N-heterocyclic carbene ligands from a theoretical viewpoint." The Journal of Physical Chemistry A 118.27 (2014): 5058-5067.*
International Search Report dated Jan. 20, 2015 for PCT/JP2014/081827.

* cited by examiner

L

L

ORGANIC ELECTROLUMINESCENT ELEMENT, LIGHTING DEVICE, AND DISPLAY DEVICE

CROSS REFERENCE TO RELATED APPLICATION

This Application is a 371 of PCT/JP2014/081827 filed on Dec. 2, 2014 which, in turn, claimed the priority of Japanese Application No. 2013-253754 filed on Dec. 9, 2013, both applications are incorporated herein by reference.

TECHNICAL FIELD

The present invention relates to an organic electroluminescent element, a lighting device, and a display device. More specifically, it relates to an organic electroluminescent element which has a shorter maximum luminescent wavelength, a long luminous lifespan, a low driving voltage, a small time-dependent change in driving voltage, and a small change in external extraction quantum efficiency even when being used at a high temperature, and the like.

BACKGROUND ART

An organic electroluminescent element (hereinafter, also referred to as the "organic EL element") has a constitution in which a luminous layer containing a luminescent compound is sandwiched between a positive electrode and a negative electrode, and it is a luminescent element utilizing the release of light (fluorescence or phosphorescence) when an exciton is generated by rebinding, in the luminous layer, a hole injected from the positive electrode with an electron injected from the negative electrode while applying an electric field and this exciton decays. In addition, an organic EL element is an all-solid-state element in which a film of an organic material having a thickness of only about submicrons is constituted between the electrodes, and it is expected to be utilized in the next generation flat display or lighting as it is able to emit light at a voltage of about several V to several tens of V.

As the development of an organic EL element for practical use, an organic EL element which utilizes phosphorescence from the excited triplet state has been reported by Princeton University, and thereafter, researches on the materials which exhibit phosphorescence at room temperature have been actively carried out. Furthermore, an organic EL element utilizing phosphorescence is able to realize a luminous efficiency of about four times that of an organic EL element utilizing fluorescence of the prior art in principle, and thus the research and development of the layer constitution or electrode of the luminescent element including the material development are being carried out all over the world.

Among them, a great number of organometallic complexes using heavy metals including iridium are investigated from the viewpoint of a high luminous efficiency and a long luminous lifespan.

For example, in Patent Literatures 1 to 3, a metal complex obtained by substituting the metal complex with a cyano group of an electron withdrawing group in order to shorten the maximum luminescent wavelength is disclosed.

However, the disclosed metal complex is still required to be improved in the chromaticity of the luminous color affected by the shape of the luminescence emission spectrum or the size of the peak or in the luminous lifespan or external extraction quantum efficiency as an organic EL element although shortening of the maximum luminescent wavelength is observed. Furthermore, a decrease in external extraction quantum efficiency is acknowledged when the disclosed metal complex is used at a high temperature.

These problems have been a major problem in the fabrication of an organic EL element which uses a metal complex substituted with a cyano group of an electron withdrawing group and has a relatively short maximum luminescent wavelength. In particular, these problems have been a major problem in the fabrication of an organic EL element which emits light in blue to blue green.

In addition, a technique utilizing a condensed aromatic ring as the ligand to directly coordinate the central metal is disclosed as a means for shortening the luminescent wavelength. For example, in Patent Literature 4, a metal complex of which the luminescent wavelength is shortened and the stability of the compound is improved by utilizing a phenanthridine backbone as a ligand has been disclosed. However, such a metal complex is not satisfactory from the viewpoint of improving the luminous efficiency as the aggregability among the complexes is strengthened.

CITATION LIST

Patent Literature

Patent Literature 1: WO 2007/29533 A
Patent Literature 2: JP 2009-96861 A
Patent Literature 3: WO 2007/29461 A
Patent Literature 4: JP 2010-215759 A

SUMMARY OF INVENTION

Technical Problem

The present invention has been made in view of the above problems and circumstances, and an object thereof is to provide an organic EL element which has a shorter maximum luminescent wavelength, a long luminous lifespan, a low driving voltage, a small time-dependent change in driving voltage, and a small change in external extraction quantum efficiency even when being used at a high temperature. In addition, an object of the present invention is to provide a lighting device and a display device including the organic EL element.

Solution to Problem

The present inventors have investigated on the factor or the like of the above problem in order to solve the above problem, and it has been found out that the problem can be solved by introducing an aromatic hydrocarbon ring group or aromatic heterocyclic ring group having an electron withdrawing group and a substituent at a specific site into the luminous layer of an organic EL element or by containing a phosphorescent organometallic complex having a structure in which at least one aromatic ring of the ligands to directly bond to a metal atom is a condensed ring in the luminous layer, thereby the present invention has been completed.

In other words, the problem according to the present invention is solved by the following means.

1. An organic electroluminescent element including: at least one luminous layer sandwiched between a positive electrode and a negative electrode, wherein the luminous layer contains at least one kind of phosphorescent organometallic complex having a structure represented by the following Formula (1):

[Chemical Formula 1]

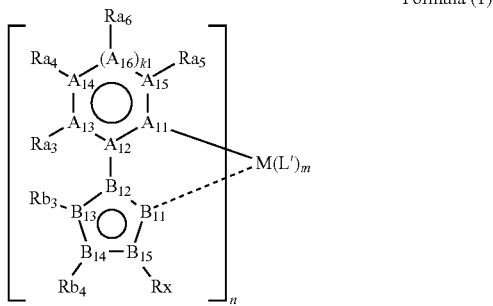

Formula (1)

(in Formula (1), a ring constituted by $A_{11}$ to $A_{16}$ represents an aromatic hydrocarbon ring or an aromatic heterocyclic ring. A ring constituted by $B_{11}$ to $B_{15}$ represents an aromatic heterocyclic ring.

$A_{11}$, $A_{12}$, and $B_{11}$ to $B_{15}$ each independently represent C or N.

$A_{13}$ to $A_{16}$ each independently represent any one of C, N, O, or S.

k1 represents an integer of 0 or 1, $A_{14}$ and $A_{15}$ are directly bonded to each other in a case in which k1 is 0.

Rx represents an electron withdrawing group.

$Ra_3$, $Ra_4$, $Ra_5$, or $Ra_6$ on O or S is not present in a case in which any one of $A_{13}$ to $A_{16}$ is O or S.

$Ra_3$, $Ra_4$, $Ra_5$, $Ra_6$, $Rb_3$, or $Rb_4$ on N is not present in some cases in a case in which any one of $A_{13}$ to $A_{16}$, $B_{13}$, or $B_{14}$ is N.

$Ra_3$ to $Ra_6$ and $Rb_4$ each represent a hydrogen atom or a substituent in a case in which $Rb_3$ represents an aromatic hydrocarbon ring having a substituent or an aromatic heterocyclic ring having a substituent. The substituents may be bonded to each other to form a ring structure. The substituent on $Rb_3$ and the substituent on $Ra_3$ to $Ra_6$ and $Rb_4$ may be the same as or different from one another.

$Rb_3$, $Rb_4$, and $Ra_3$ to $Ra_6$ each represent a hydrogen atom or a substituent in a case in which $Rb_3$ is not an aromatic hydrocarbon ring having a substituent or an aromatic heterocyclic ring having a substituent, but at least any one pair of two adjacent substituents among $Rb_3$, $Rb_4$ and Rx, or $Ra_3$ to $Ra_6$ are bonded to each other to form a ring structure.

M represents iridium or platinum.

L' represents a monoanionic bidentate ligand.

n represents an integer from 1 to 3, and m represents an integer from 0 to 2).

2. The organic electroluminescent element according to Item. 1, wherein Rx in the phosphorescent organometallic complex of Formula (1) represents a cyano group.

3. The organic electroluminescent element according to Item. 1 or 2, wherein the aromatic heterocyclic ring constituted by $B_{11}$ to $B_{15}$ is an imidazole ring.

4. The organic electroluminescent element according to Item. 1 or 2, wherein the aromatic heterocyclic ring constituted by $B_{11}$ to $B_{15}$ is a pyrazole ring.

5. The organic electroluminescent element according to Item. 1 or 2, wherein the aromatic heterocyclic ring constituted by $B_{11}$ to $B_{15}$ is a triazole ring.

6. The organic electroluminescent element according to any one of Items. 1 to 5, wherein a substituent represented by $Ra_3$ in the phosphorescent organometallic complex represented by Formula (1) is a fluorine atom.

7. The organic electroluminescent element according to any one of Items. 1 to 6, including at least one luminescent dopant exhibiting a luminous color different from the luminous color of the phosphorescent organometallic complex in addition to the phosphorescent organometallic complex represented by Formula (1) and emitting light in white.

8. A lighting device including the organic electroluminescent element according to any one of Items. 1 to 7.

9. A display device including the organic electroluminescent element according to any one of Items. 1 to 7.

Advantageous Effects of Invention

By the above means of the present invention, it is possible to provide an organic EL element which has a shorter maximum luminescent wavelength, a long luminous lifespan, a low driving voltage, a small time-dependent change in driving voltage, and a small change in external extraction quantum efficiency even when being used at a high temperature. In addition, it is possible to provide a lighting device and a display device including the element.

Incidentally, in the present invention, an organic EL element having a shorter maximum luminescent wavelength refers to an organic EL element which has an electron withdrawing group introduced into a metal complex and preferably which emits light in blue to blue green in a maximum luminescent wavelength range of from 380 to 520 nm.

The mechanism of exertion or action of the effect of the present invention has not been clear, but it is presumed as follows.

With regard to the shortening of the maximum luminescent wavelength of a phosphorescent organometallic complex, it is known that an electron withdrawing group such as a cyano group is introduced into a ligand as it has been disclosed in Patent Literatures 1 to 3 described above.

The shortening of the maximum luminescent wavelength by introduction of an electron withdrawing group has also been investigated for the metal complex represented by Formula (1) of the present invention, and it has been found that the effect varies depending on the site to be introduced.

For example, it has been found that the maximum luminescent wavelength is not shortened but rather strongly tends to be lengthened when an electron withdrawing group is introduced into the position of $Rb_4$ in Formula (1) and also the effect varies depending on the kind of the aromatic heterocyclic ring constituted by $B_{11}$ to $B_{15}$ in the introduction of an electron withdrawing group into the position of $Rb_3$.

On the other hand, it has been found that the maximum luminescent wavelength is shortened regardless of the kind of the aromatic heterocyclic ring constituted by $B_{11}$ to $B_{15}$ in the introduction of an electron withdrawing group into the position of Rx in Formula (1). It is assumed that this is because it is possible to effectively withdraw an electron from the central metal by introducing an electron withdrawing group into an atom adjacent to the atom ($B_{11}$ in Formula (1)) that is bonded to the central metal.

In addition, it has been found that it is possible to suppress the vibration structure of the metal complex by the steric effect when a substituent is introduced into the position of Rx and thus the luminescence emission spectrum tends to be sharpened (decrease in half width).

In other words, it is possible to improve shortening of the maximum luminescent wavelength together with the shape of the luminescence emission spectrum and to obtain a metal complex emitting light in blue with more favorable chromaticity by introducing an electron withdrawing group into the position of Rx. However, the improvement of only the maximum luminescent wavelength is insufficient as the performance of an organic EL element.

One of the problems of the phosphorescent metal complex used in an organic EL element includes the aggregability (or association properties) of the metal complex. The aggregation of the metal complex in the luminous layer causes a decrease in the luminous efficiency by the triplet-triplet annihilation (T-T annihilation) or lengthening of the maximum luminescent wavelength, and thus the performance of the metal complex composed of a single molecule cannot be effectively exerted.

Hence, in the present invention, it is possible to suppress the aggregation of the metal complex by introducing an aromatic hydrocarbon ring or aromatic heterocyclic ring having a substituent into the $Rb_3$ site in Formula (1). It is considered that this is because an aromatic hydrocarbon ring or aromatic heterocyclic ring having a substituent is sterically large, and thus approaching of the metal complexes to one another can be suppressed.

In other words, it has been found that the effect of improving the chromaticity of the luminous color is also obtained by the introduction of an aromatic hydrocarbon ring or aromatic heterocyclic ring having a substituent into $Rb_3$ in addition to the effect of an electron withdrawing group described above, and further, the effect of improving a decrease in the luminous efficiency is obtained.

On the other hand, it is possible to sharpen the luminescence emission spectrum by forming at least either of a ring constituted by $A_{11}$ to $A_{16}$ or a ring constituted by $B_{11}$ to $B_{15}$ into a condensed ring in a case in which $Rb_3$ is not an aromatic hydrocarbon ring having a substituent or an aromatic heterocyclic ring.

This is because a change of the steric structure in the ground state and the excited state is suppressed as the ring is condensed, and as a result, it is possible to obtain a sharp waveform in the luminescence emission spectrum since a change of the steric structure in the ground state and the excited state is small.

Furthermore, it has been found that the effect of improving a decrease in external extraction quantum efficiency is obtained. It is estimated that this is because the structural change described above is small.

However, the flatness increases and the aggregability among the metal complexes is too strengthened as the flat site spreads when the ligand takes one condensed ring structure, and thus it is preferable that the condensed ring structure is formed by the bonding of $Rb_3$ and $Rb_4$ or two adjacent groups among $Ra_3$ to $Ra_6$.

As described above, the effect of suppressing the structural change obtained as an aromatic hydrocarbon ring or aromatic heterocyclic ring having a substituent is introduced into $Rb_3$ or at least either of a ring constituted by $A_{11}$ to $A_{16}$ or a ring constituted by $B_{11}$ to $B_{15}$ forms a condensed ring is also effective in improving the external extraction quantum efficiency or the driving voltage at the time of driving the organic EL element and the luminous lifespan. In particular, a change in external extraction quantum efficiency at a high temperature is greatly improved. It is estimated that this is because the vibration level is likely to be affected by the temperature of the external environment in general.

DESCRIPTION OF EMBODIMENTS

Figure 1:
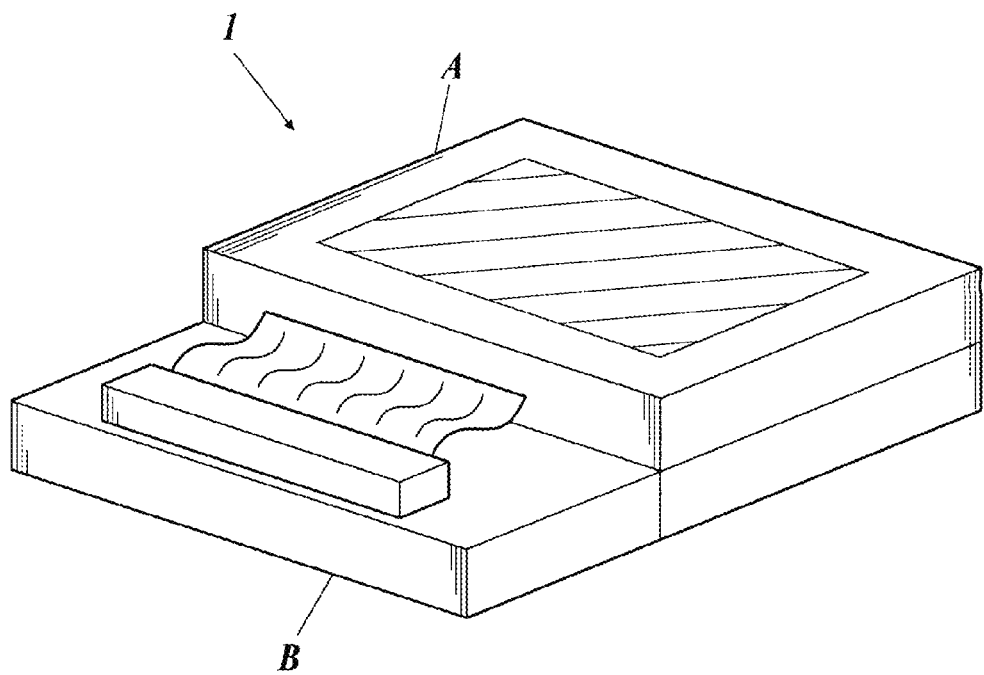
FIG. 1 is a schematic view illustrating an example of a display device constituted by an organic EL element.

An organic electroluminescent element of the present invention is an organic electroluminescent element which has at least one luminous layer sandwiched between a positive electrode and a negative electrode and is characterized in that the luminous layer contains at least one kind of phosphorescent organometallic complex having a structure represented by Formula (1) above. This characteristic is a technical feature that is common to the invention according to claims 1 to 9.

As an embodiment of the present invention, it is preferable that Rx in the phosphorescent organometallic complex of Formula (1) above represents a cyano group. A cyano group has the bulkiness of a substituent which is suitable for suppressing the structural variation of the metal complex and exhibits electron withdrawing properties, and thus an effect of achieving both the shape change of the luminescence emission spectrum and the shortening of the maximum luminescent wavelength is obtained.

In addition, it is preferable that the aromatic heterocyclic ring constituted by $B_{11}$ to $B_{15}$ is an imidazole ring, a pyrazole ring, or a triazole ring since an effect of decreasing the distortion of the structure of the metal complex is obtained.

Furthermore, in the present invention, it is preferable that the substituent represented by $Ra_3$ in the phosphorescent organometallic complex represented by Formula (1) above is a fluorine atom since an effect of shortening the maximum luminescent wavelength is obtained.

In addition, it is preferable that the organic EL element of the present invention contains at least one luminescent dopant exhibiting a luminous color different from the luminous color of the phosphorescent organometallic complex in addition to the phosphorescent organometallic complex represented by Formula (1) and emits light in white.

The organic EL element of the present invention can be suitably included in a lighting device and a display device.

Hereinafter, the present invention and its constituents, and the form and mode for carrying out the present invention will be described in detail. Incidentally, in the present application, the term to is used in the sense of including the numerical values described before and after the term to as the lower limit value and the upper limit value, respectively.

<<Overview of Organic Electroluminescent Element>>

The organic electroluminescent element of the present invention is an organic electroluminescent element which has at least one luminous layer sandwiched between a positive electrode and a negative electrode and is characterized in that the luminous layer contains at least one kind of phosphorescent organometallic complex having a structure represented by Formula (1) above.

Hereinafter, the constitution of the organic electroluminescent element will be described in detail.

<<Phosphorescent Organometallic Complex Represented by Formula (1)>>

The organic EL element of the present invention contains at least one kind of phosphorescent organometallic complex having a structure represented by the following Formula (1) in the luminous layer.

[Chemical Formula 2]

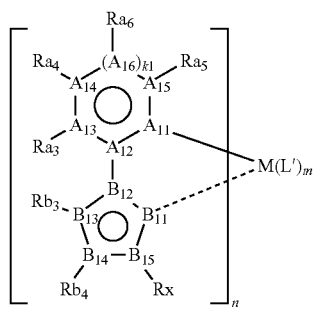

Formula (1)

In Formula (1), a ring constituted by $A_{11}$ to $A_{16}$ represents an aromatic hydrocarbon ring or an aromatic heterocyclic ring. A ring constituted by $B_{11}$ to $B_{15}$ represents an aromatic heterocyclic ring.

$A_{11}$, $A_{12}$, and $B_{11}$ to $B_{15}$ each independently represent C or N.

$A_{13}$ to $A_{16}$ each independently represent any one of C, N, O, or S.

k1 represents an integer of 0 or 1, $A_{14}$ and $A_{15}$ are directly bonded to each other in a case in which k1 is 0.

Rx represents an electron withdrawing group.

$Ra_3$, $Ra_4$, $Ra_5$, or $Ra_6$ on O or S is not present in a case in which any one of $A_{13}$ to $A_{16}$ is O or S.

$Ra_3$, $Ra_4$, $Ra_5$, $Ra_6$, $Rb_3$, or $Rb_4$ on N is not present in some cases in a case in which any one of $A_{13}$ to $A_{16}$, $B_{13}$, or $B_{14}$ is N.

$Ra_3$ to $Ra_6$ and $Rb_4$ each represent a hydrogen atom or a substituent in a case in which $Rb_3$ represents an aromatic hydrocarbon ring having a substituent or an aromatic heterocyclic ring having a substituent. The substituents may be bonded to each other to form a ring structure. The substituent on $Rb_3$ and the substituent on $Ra_3$ to $Ra_6$ and $Rb_4$ may be the same as or different from one another.

$Rb_3$, $Rb_4$, and $Ra_3$ to $Ra_6$ each represent a hydrogen atom or a substituent in a case in which $Rb_3$ is not an aromatic hydrocarbon ring having a substituent or an aromatic heterocyclic ring having a substituent, but at least any one pair of two adjacent substituents among $Rb_3$, $Rb_4$ and Rx, or $Ra_3$ to $Ra_6$ are bonded to each other to form a ring structure.

M represents iridium or platinum.

L' represents a monoanionic bidentate ligand.

n represents an integer from 1 to 3, and m represents an integer from 0 to 2.

The groups represented by $Ra_3$ to $Ra_6$, $Rb_3$, and $Rb_4$, represent any group selected from a hydrogen atom, a halogen atom (for example, a chlorine atom, a bromine atom, an iodine atom, or a fluorine atom), a cyano group, an alkyl group (for example, a methyl group, an ethyl group, a propyl group, an isopropyl group, a (t)butyl group, a pentyl group, a hexyl group, an octyl group, a dodecyl group, a tridecyl group, a tetradecyl group, a pentadecyl group, or a benzyl group), an alkenyl group (for example, a vinyl group or an allyl group), an alkynyl group (for example, a propargyl group), an alkoxy group (for example, a methoxy group, an ethoxy group, a propyloxy group, a pentyloxy group, a hexyloxy group, an octyloxy group, or a dodecyl group), an aryloxy group (for example, a phenoxy group or a naphthyloxy group), an alkylthio group (for example, a methylthio group, an ethylthio group, a propylthio group, a pentylthio group, a hexylthio group, an octylthio group, or a dodecylthio group), an arylthio group (for example, a phenylthio group or a naphthylthio group), an amino group (for example, an amino group, an ethylamino group, a dimethylamino group, a butylamino group, a cyclopentylamino group, a 2-ethylhexyl group, a dodecyl group, an anilino group, a diarylamino group (for example, a diphenylamino group, a dinaphthylamino group, or a phenylnaphthylamino group), a naphthylamino group, or a 2-pyridylamino group), a silyl group (for example, a trimethylsilyl group, a triethylsilyl group, a (t)butyldimethylsilyl group, a triisopropylsilyl group, a (t)butyldiphenylsilyl group, a triphenylsilyl group, a trinaphthylsilyl group, or a 2-pyridylsilyl group), a phosphino group (a dimethylphosphino group, a diethylphosphino group, a dicyclohexylphosphino group, a methylphenylphosphino group, a diphenylphosphino group, a dinaphthylphosphino group, or a di(2-pyridyl)phosphino group), a phosphoryl group (a dimethylphosphoryl group, a diethylphosphoryl group, a dicyclohexylphosphoryl group, a methylphenylphosphoryl group, a diphenylphosphoryl group, a dinaphthylphosphoryl group, or a di(2-pyridyl)phosphoryl group), an aryl group (for example, a phenyl group, a p-chlorophenyl group, a mesityl group, a tolyl group, a xylyl group, a naphthyl group, an anthryl group, an azulenyl group, an acenaphthenyl group, a fluorenyl group, a phenanthryl group, an indenyl group, a pyrenyl group, or a biphenylyl group), a heteroaryl group (a pyridyl group, a pyrimidinyl group, a furyl group, a pyrrolyl group, an imidazolyl group, a benzimidazolyl group, a pyrazolyl group, a pyrazinyl group, a triazolyl group (for example, a 1,2,4-triazol-1-yl group or a 1,2,3-triazol-1-yl group), an oxazolyl group, a benzoxazolyl group, a thiazolyl group, an isoxazolyl group, an isothiazolyl group, a furazanyl group, a thienyl group, a quinolyl group, a benzofuryl group, a dibenzofuryl group, a benzothienyl group, a dibenzothienyl group, an indolyl group, an indoloindolyl group, a carbazolyl group, or a carbolinyl group, a diazacarbazolyl group (indicating one obtained by substituting one of the carbon atoms constituting the carboline ring of the carbolinyl group with a nitrogen atom), a quinoxalinyl group, a pyridazinyl group, a triazinyl group, a quinazolinyl group, or a phthalazinyl group), a cycloalkoxyl group (for example, a cyclopentyloxy group or a cyclohexyloxy group), a non-aromatic hydrocarbon ring group (for example, a cycloalkyl group (for example, a cyclopentyl group or a cyclohexyl group), a cycloalkylthio group (for example, a cyclopentylthio group or a cyclohexylthio group), a cyclohexylaminosulfonyl group, a tetrahydronaphthyl group, a 9,10-dihydroanthryl group, or a biphenylyl group), and a non-aromatic heterocyclic group (for example, an epoxy ring, an aziridine ring, a thiirane ring, an oxetane ring, an azetidine ring, a thiethane ring, a tetrahydrofuran ring, a dioxolane ring, a pyrrolidine ring, a pyrazolidine ring, an imidazolidine ring, an oxazolidine ring, a tetrahydrothiophene ring, a sulfolane ring, a thiazolidine ring, an ε-caprolactone ring, an ε-caprolactam ring, a piperidine ring, a hexahydropyridazine ring, a hexahydropyrimidine ring, a piperazine ring, a morpholine ring, a tetrahydropyran ring, a 1,3-dioxane ring, a 1,4-dioxane ring, a trioxane ring, a tetrahydrothiopyran ring, a thiomorpholine ring, a thiomorpholine-1,1-dioxide ring, a pyranose ring, or a diazabicyclo[2,2,2]octane ring). Here, the groups other than the hydrogen atom are referred to as a substituent. Incidentally, these substituents may further have the substituent described above.

In a case in which $Rb_3$ is an aromatic hydrocarbon ring having a substituent, examples of the aromatic hydrocarbon ring may include a benzene ring, a biphenyl ring, a naphthalene ring, an azulene ring, an anthracene ring, a phenanthrene ring, a pyrene ring, a chrysene ring, a naphthacene ring, a triphenylene ring, an o-terphenyl ring, a m-terphenyl ring, a p-terphenyl ring, an acenaphthene ring, a coronene ring, a fluorene ring, a fluoranthrene ring, a naphthacene ring, a pentacene ring, a perylene ring, a pentaphene ring, a picene ring, a pyrene ring, a pyranthrene ring, and an anthranthrene ring.

In particular, a benzene ring having a substituent is preferable.

In a case in which $Rb_3$ is an aromatic heterocyclic ring having a substituent, examples of the aromatic heterocyclic ring may include a silole ring, a furan ring, a thiophene ring, an oxazole ring, a pyrrole ring, a pyridine ring, a pyridazine ring, a pyrimidine ring, a pyrazine ring, a triazine ring, an oxadiazole ring, a triazole ring, an imidazole ring, a pyrazole ring, a thiazole ring, an indole ring, a benzimidazole ring, a benzothiazole ring, a benzoxazole ring, a quinoxaline ring, a quinazoline ring, a phthalazine ring, a thienothiophene ring, a carbazole ring, an azacarbazole ring (representing one obtained by substituting one or more arbitrary carbon atoms among the carbon atoms constituting a carbazole ring with a nitrogen atom), a dibenzosilole ring, a dibenzofuran ring, a dibenzothiophene ring, a ring obtained by substituting one or more arbitrary carbon atoms among the carbon atoms constituting a benzothiophene ring or a dibenzofuran ring with a nitrogen atom, a benzodifuran ring, a benzodithiophene ring, an acridine ring, a benzoquinoline ring, a phenazine ring, a phenanthridine ring, a phenanthroline ring, a cyclazine ring, a quindoline ring, a thebenidine ring, a quinindoline ring, a triphenodithiazine ring, a triphenodioxazine ring, a phenanthrazine ring, an anthrazine ring, a perimidine ring, a naphthofuran ring, a naphthothiophene ring, a naphthodifuran ring, a naphthodithiophene ring, an anthrafuran ring, an anthradifuran ring, an anthrathiophene ring, an anthradithiophene ring, a thianthrene ring, a phenoxathiin ring, a dibenzocarbazole ring, an indolocarbazole ring, and dithienobenzene ring.

Examples of the substituent on the aromatic hydrocarbon ring or aromatic heterocyclic ring may include the same ones as the substituents represented by $Ra_3$ to $Ra_6$, $Rb_3$, and $Rb_4$ above. An alkyl group or an alkoxy group is preferable among these.

In a case in which $Rb_3$ is not an aromatic hydrocarbon ring having a substituent or an aromatic heterocyclic ring, $Rb_3$, $Rb_4$, and $Ra_3$ to $Ra_6$ each represent a hydrogen atom or a substituent, but at least any one pair of two adjacent substituents among $Rb_3$, $Rb_4$ and Rx, or $Ra_3$ to $Ra_6$ are bonded to each other to form a ring structure.

Examples of the ring structure formed as at least any one pair of two adjacent substituents among $Rb_3$, $Rb_4$ and Rx, or $Ra_3$ to $Ra_6$ are bonded to each other may include a benzene ring, a naphthalene ring, or a phenanthrene ring as an aromatic hydrocarbon ring, a cycloalkane ring (for example, a cyclopentanone ring or a cyclohexane ring) as a non-aromatic hydrocarbon ring, and (for example, a furan ring, a thiophene ring, a pyrrole ring, an oxazole ring, a pyrrolidine ring, an imidazolidine ring, a morpholine ring, an oxazoline ring, an indole ring, or a benzofuran ring) as a heterocyclic ring. These may have a substituent. Examples of the substituent may include the substituents represented by $Ra_3$ to $Ra_6$, $Rb_3$, and $Rb_4$ above.

Particularly preferably, a benzene ring, an indole ring, a benzofuran ring are preferable.

In addition, it is preferable that the substituent represented by $Ra_3$ is a fluorine atom since an effect of shortening the maximum luminescent wavelength is obtained.

It is preferable that the substituent represented by $Ra_6$ is an electron donating group (for example, an alkyl group (a methyl group, an i-propyl group, or the like)) since an effect of shortening the maximum luminescent wavelength is obtained.

Examples of the electron withdrawing group represented by Rx may include a cyano group, a halogen (for example, a fluorine atom), a nitro group, a fluorine atom-containing substituent (for example, a fluorine-substituted alkyl group (for example, a trifluoromethyl group)), an imino group, a sulfonyl group (for example, a benzenesulfonyl group), a sulfinyl group (for example, a methylsulfinyl group), a carbonyl group (for example, a butoxycarbonyl group), a phosphine oxide group (for example, a dimethylphosphine oxide group or a diphenylphosphine oxide group), and an amide group (for example, a morpholinocarbonyl group).

A fluorine atom, a fluorine atom-containing substituent, a nitro group, and a cyano group are preferable. A cyano group is particularly preferable.

In addition, Rx and $Rb_4$ may be bonded to each other to form a ring structure in a case in which $Rb_3$ is not an aromatic hydrocarbon ring having a substituent or an aromatic heterocyclic ring having a substituent.

k1 represents an integer of 0 or 1. It is preferable that k1 represents 1. This is preferable since an effect of decreasing the distortion of the structure of the metal complex is obtained.

The monoanionic bidentate ligand that is represented by L' in Formula (1) and coordinates M is not particularly limited, but specific examples thereof may include the ligands represented by the following Formulas.

[Chemical Formula 3]

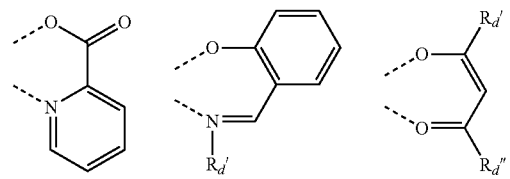

-continued

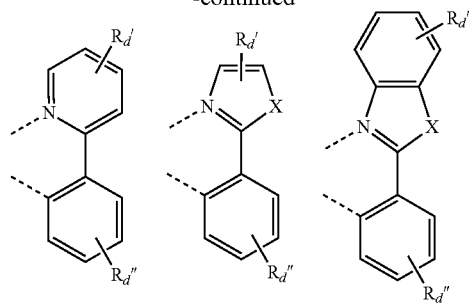

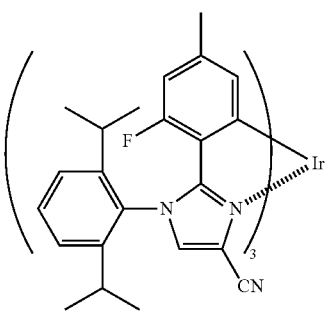

Compound 2

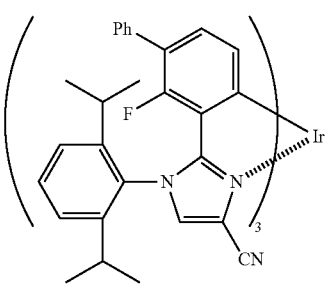

Compound 3

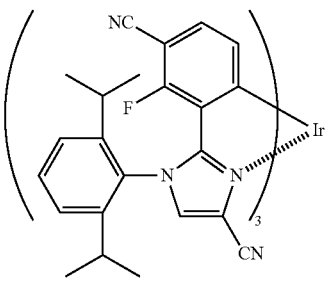

Compound 4

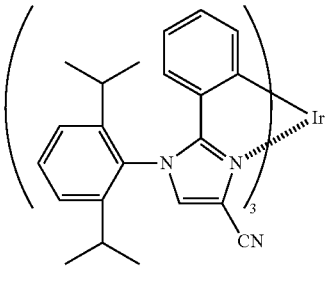

Compound 5

In Formulas above, Rd', Rd", and Rd'" represent a hydrogen atom or a substituent. Examples of the substituent may include the substituents represented by $Ra_3$ to $Ra_6$, $Rb_3$, and $Rb_4$ above. X represents N, O, or S.

n represents an integer from 1 to 3, m represents an integer from 0 to 2. It is preferable that m is 0 from the viewpoint of exertion of the effect of the present invention.

Specific examples of the phosphorescent metal complex represented by Formula (1) are presented below, but the present invention is not limited thereto.

[Chemical Formula 4]

Compound 1

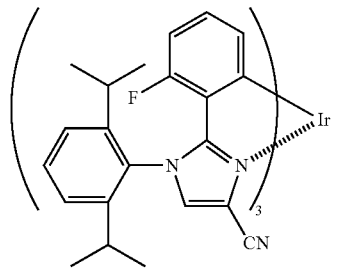

Compound 6

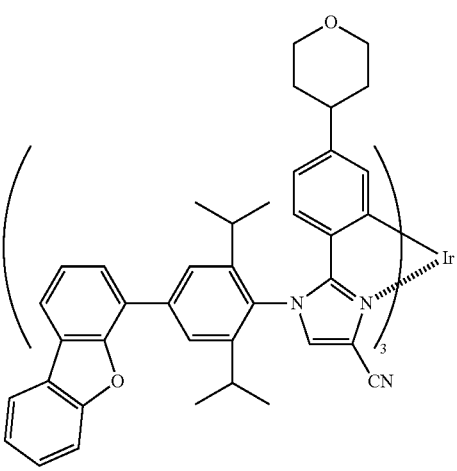

Compound 7
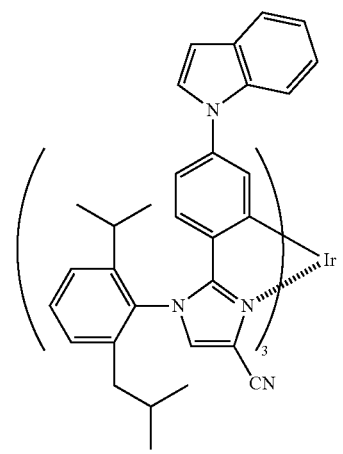
Compound 8
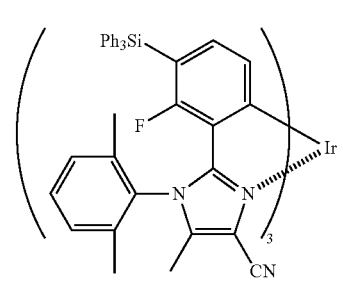
Compound 9
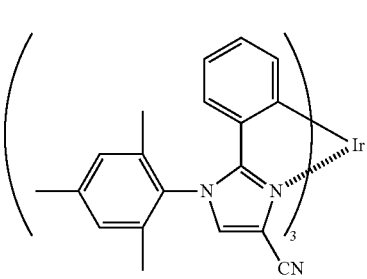
Compound 10
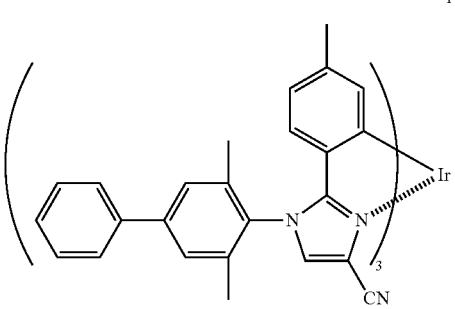
Compound 11
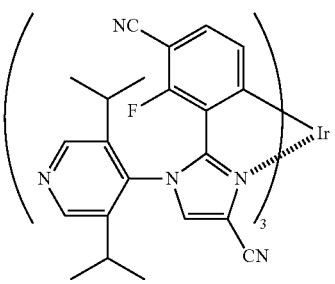
[Chemical Formula 5]
Compound 12
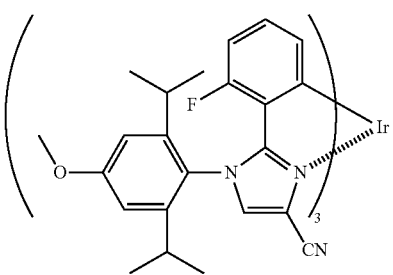
Compound 13
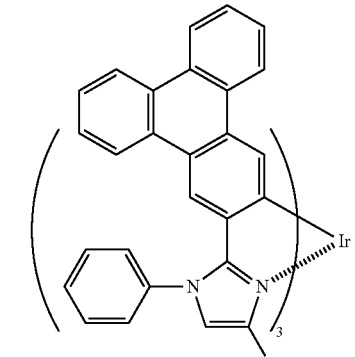
Compound 14
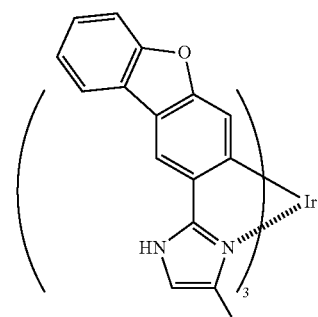
Compound 15
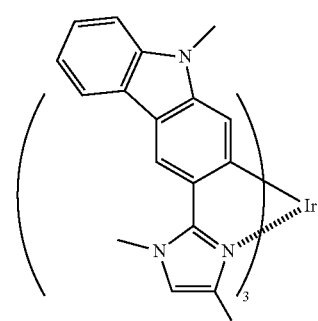

-continued
Compound 16
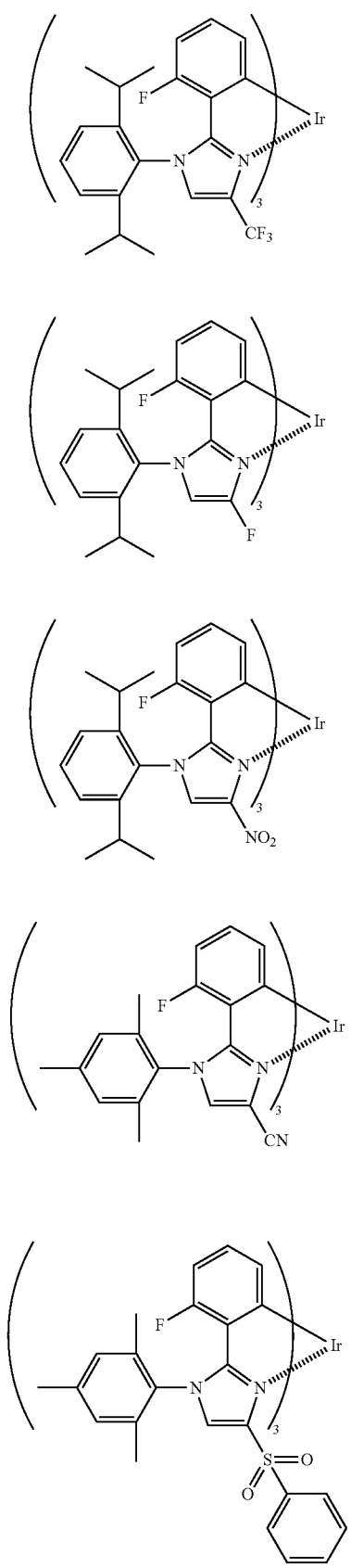
Compound 17
Compound 18
Compound 19
Compound 20
[Chemical Formula 6]
Compound 21
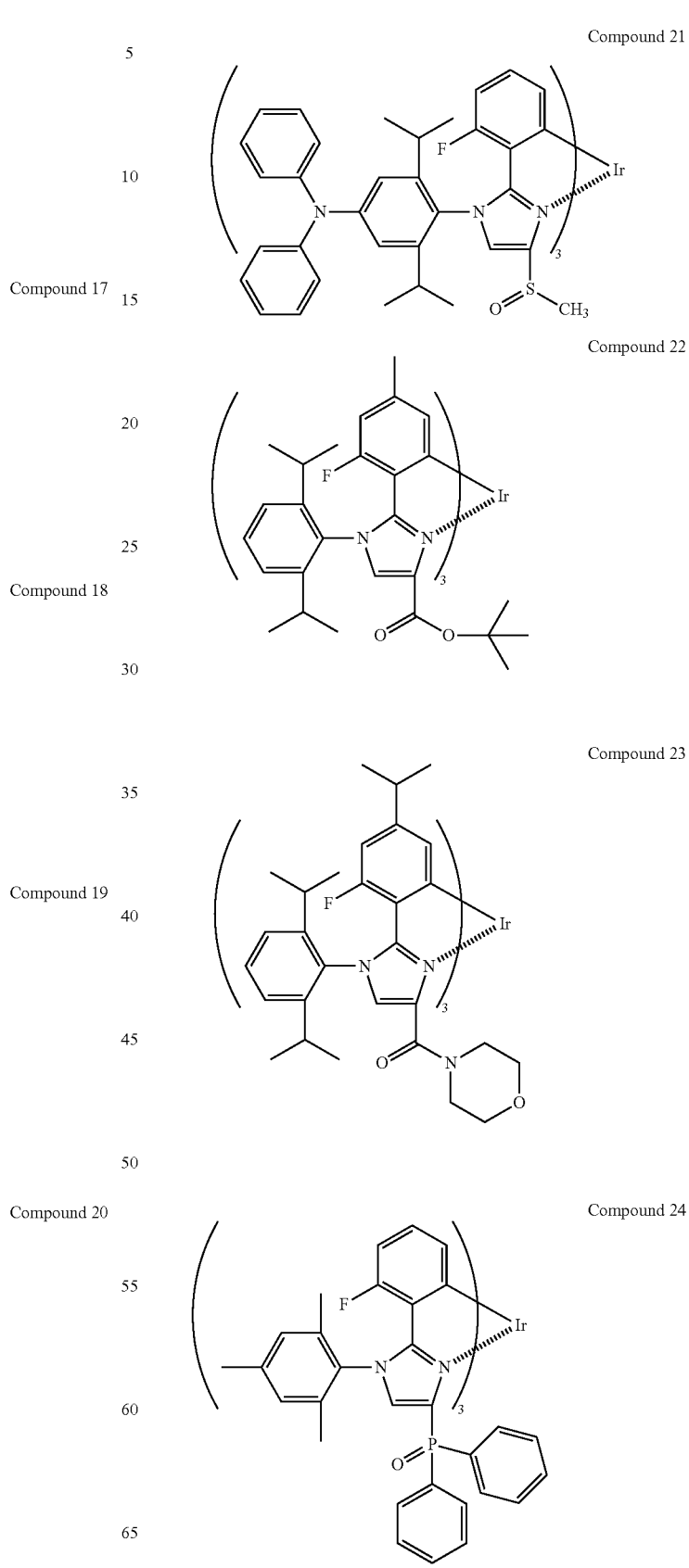
Compound 22
Compound 23
Compound 24

Compound 25
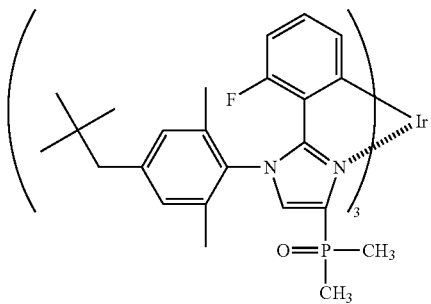
Compound 26
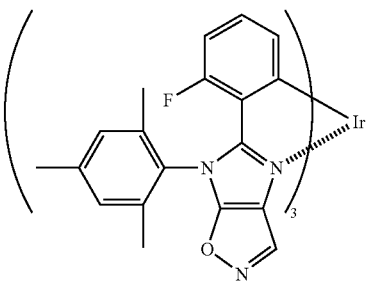
Compound 27
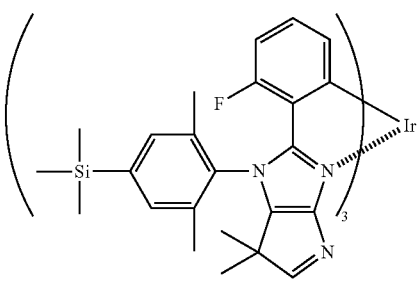
Compound 28
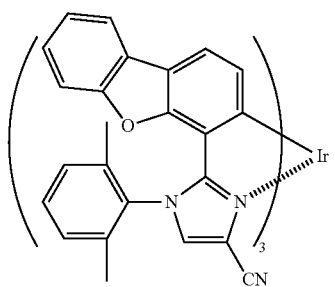
[Chemical Formula 7]
Compound 29
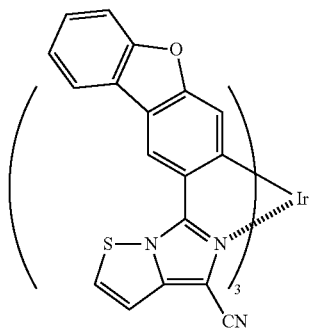
Compound 30
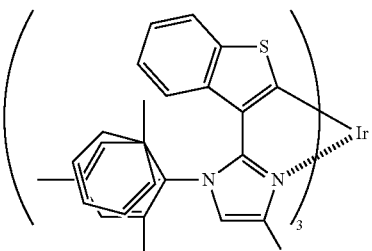
Compound 31
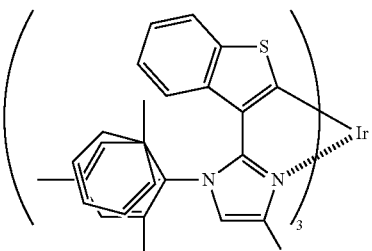
Compound 32
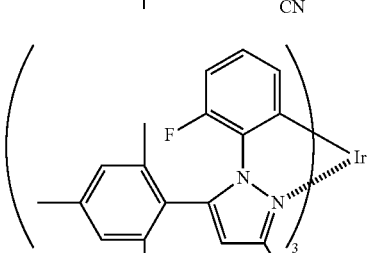
Compound 33
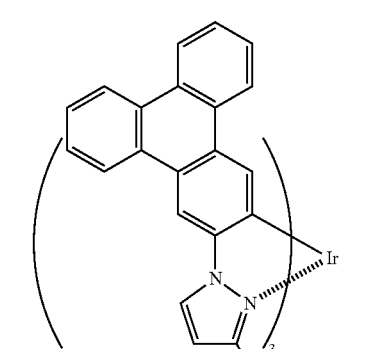
Compound 34
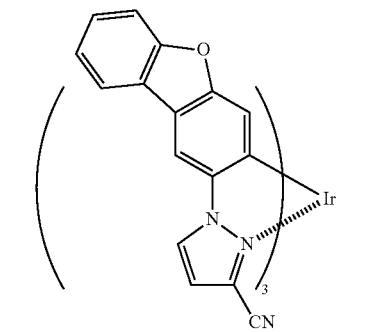

-continued
Compound 35
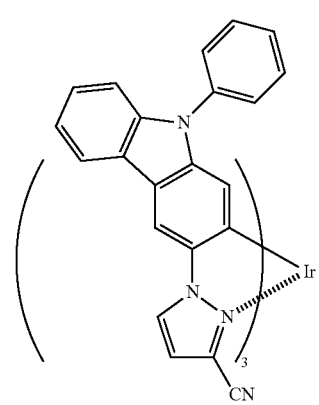
Compound 36
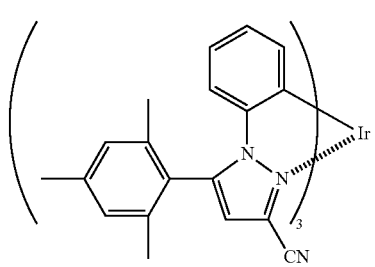
Compound 37
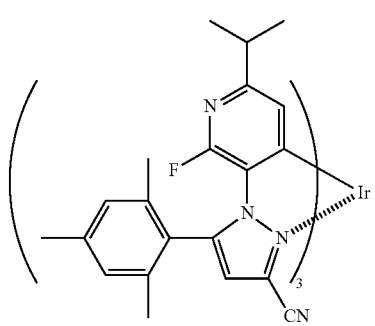
Compound 38
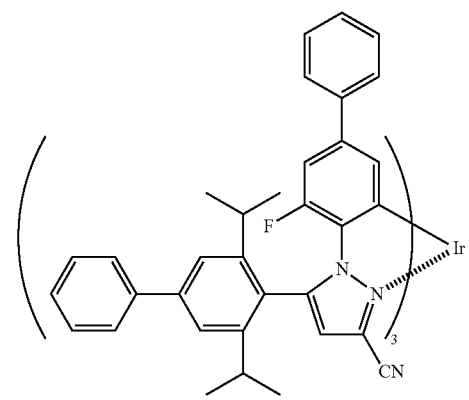
-continued
Compound 39
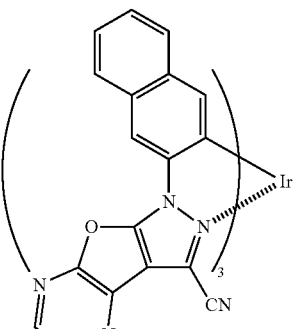
[Chemical Formula 8]
Compound 40
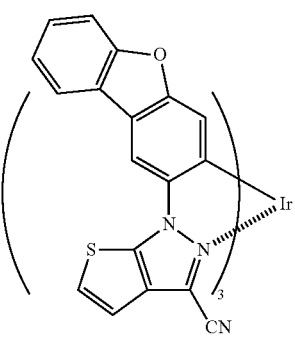
Compound 41
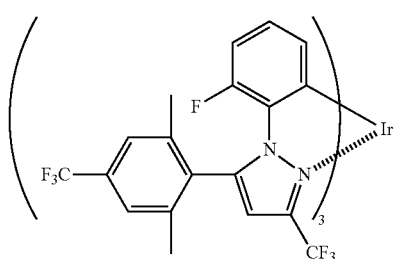
Compound 42
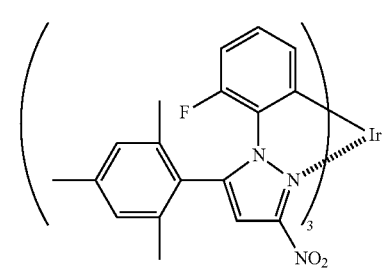
Compound 43
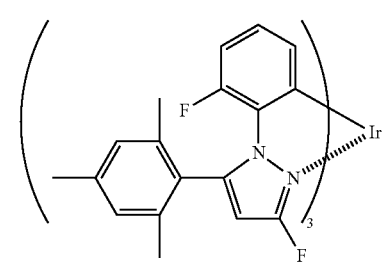

Compound 44
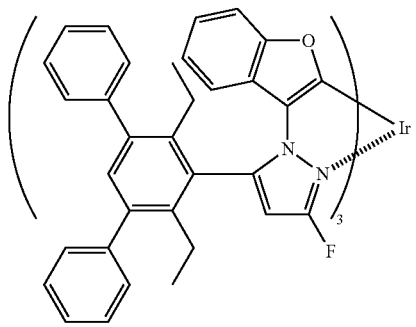
Compound 45
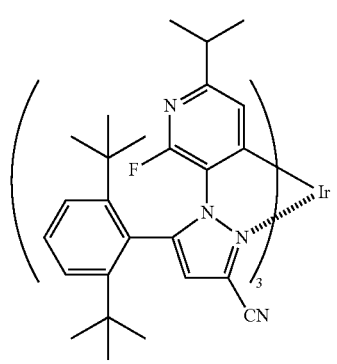
Compound 46
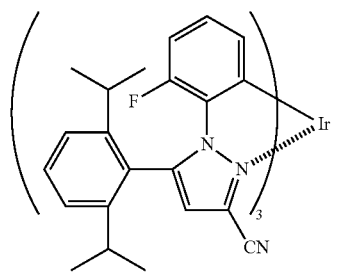
Compound 47
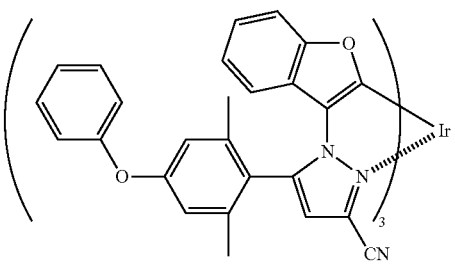
Compound 48
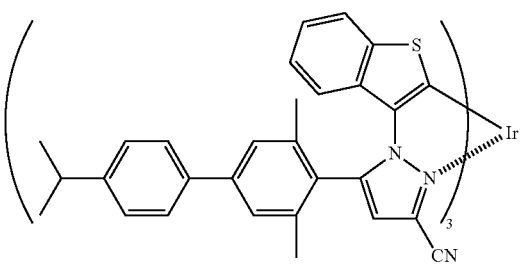
[Chemical Formula 9]
Compound 49
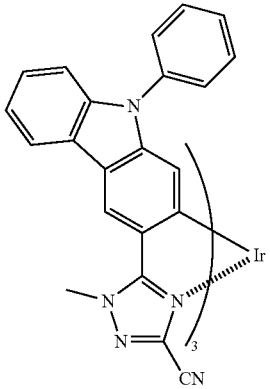
Compound 50
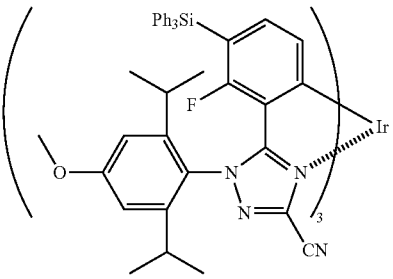
Compound 51
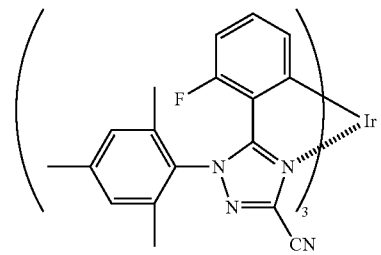
Compound 52
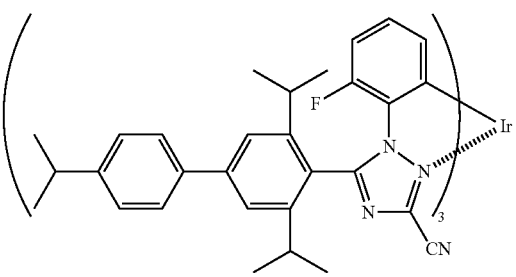
Compound 53
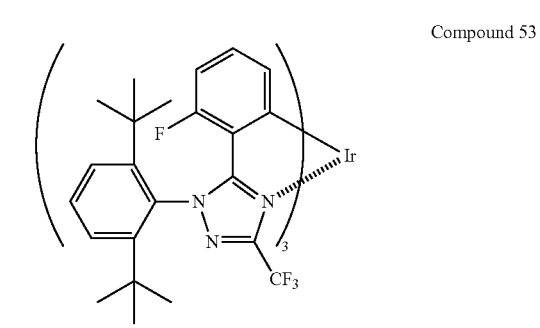

Compound 54
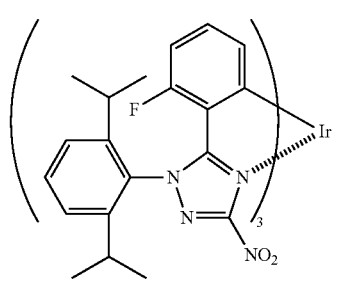
Compound 55
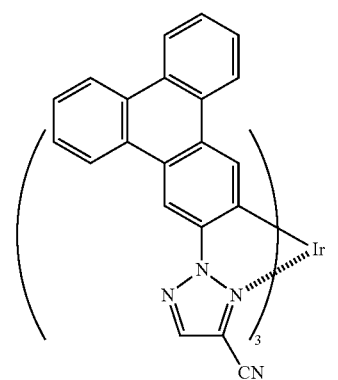
Compound 56
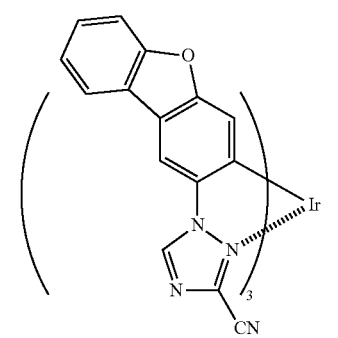
[Chemical Formula 10]
Compound 57
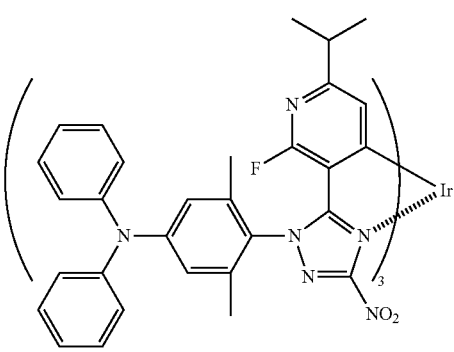
Compound 58
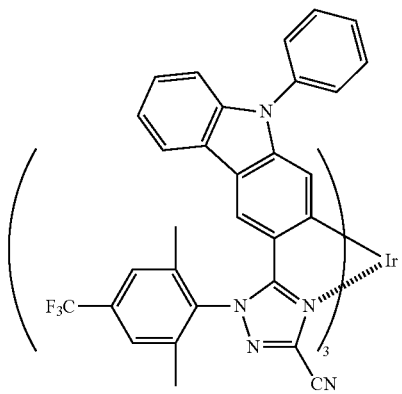
Compound 59
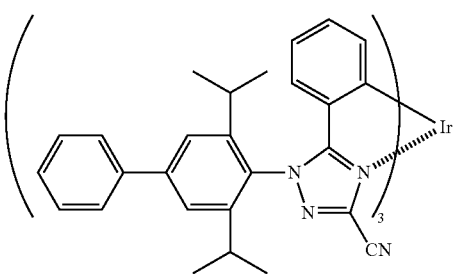
Compound 60
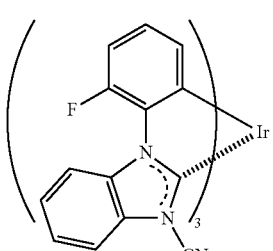
Compound 61
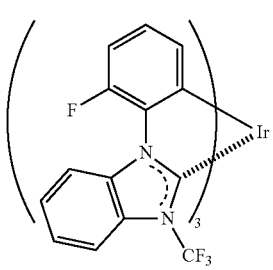
Compound 62

Compound 63
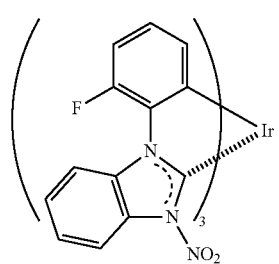
Compound 64
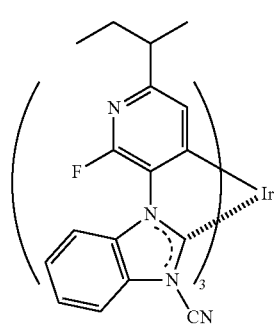
Compound 65
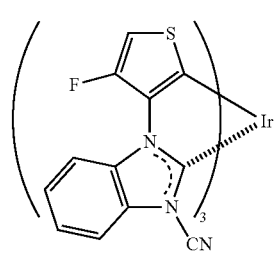
[Chemical Formula 11]
Compound 66
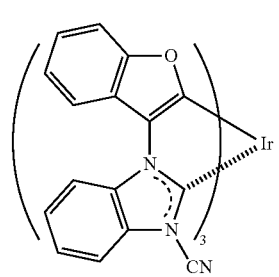
Compound 67
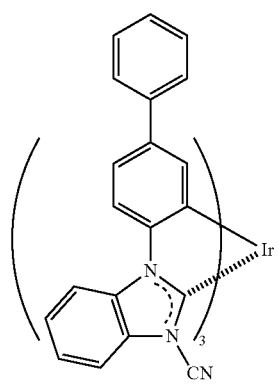
Compound 68
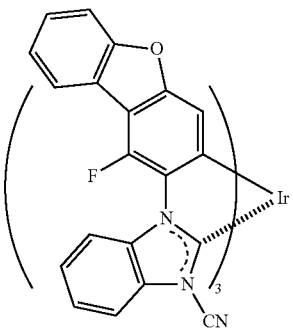
Compound 69
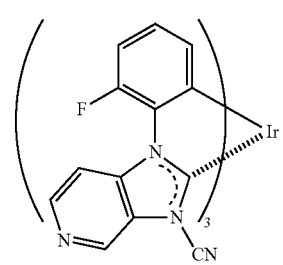
Compound 70
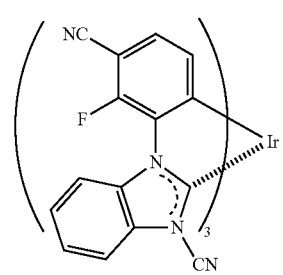
Compound 71
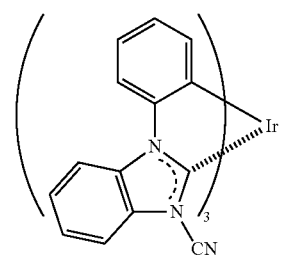
Compound 72
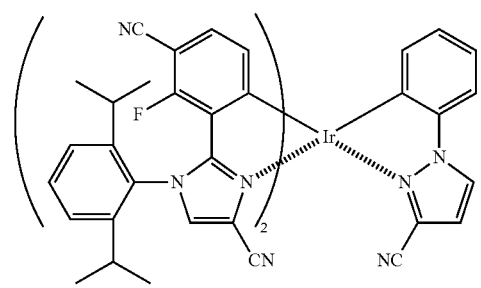

Compound 73
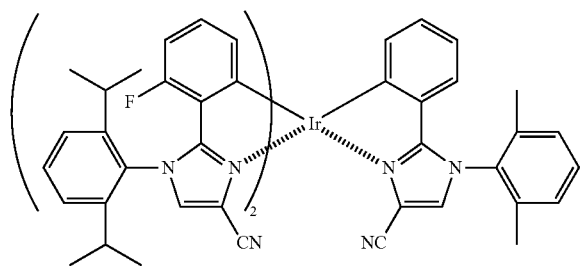
[Chemical Formula 12]
Compound 74
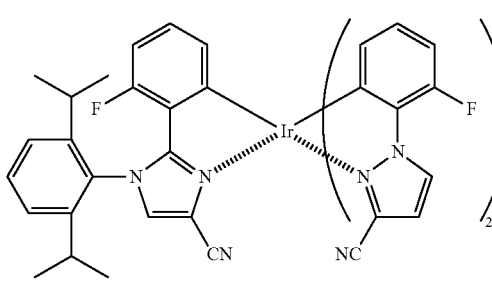
Compound 75
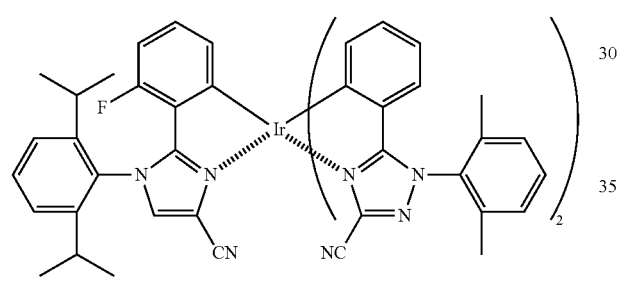
Compound 76
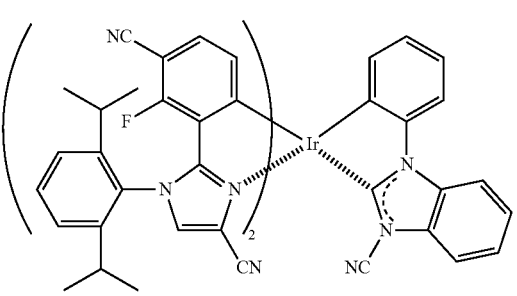
Compound 77
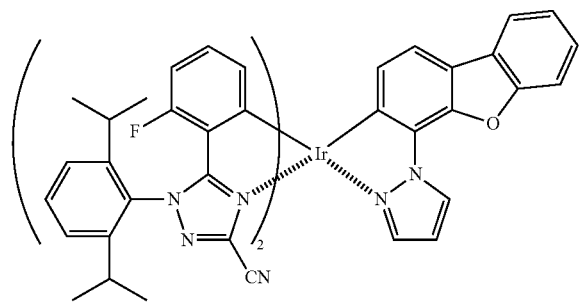
Compound 78
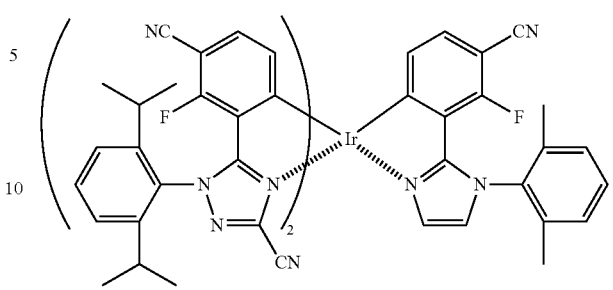
[Chemical Formula 13]
Compound 79
Compound 80
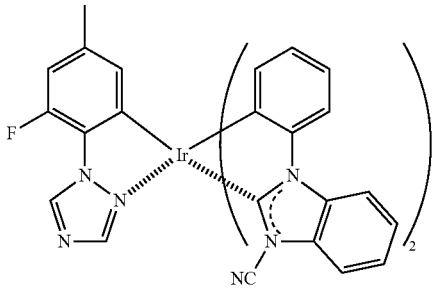
Compound 81
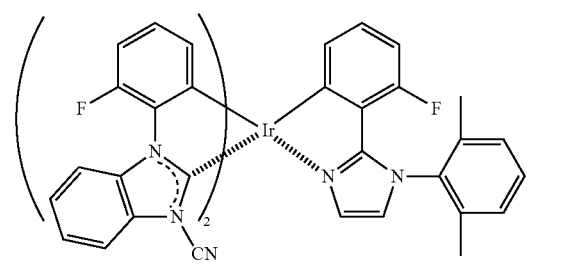
Compound 82
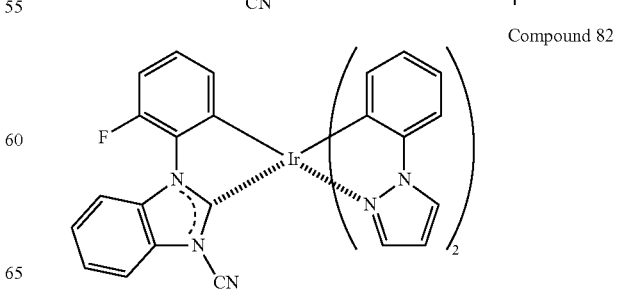

Compound 83
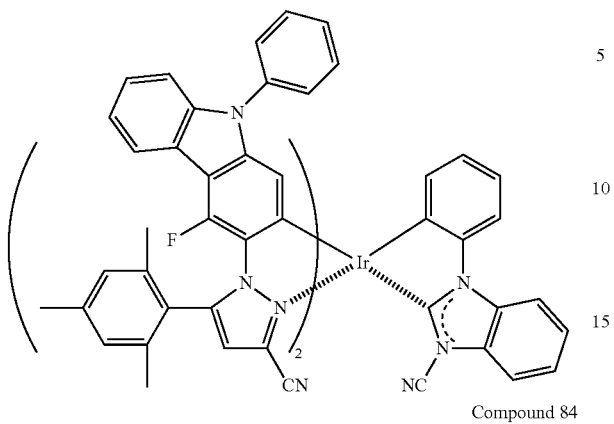
Compound 84
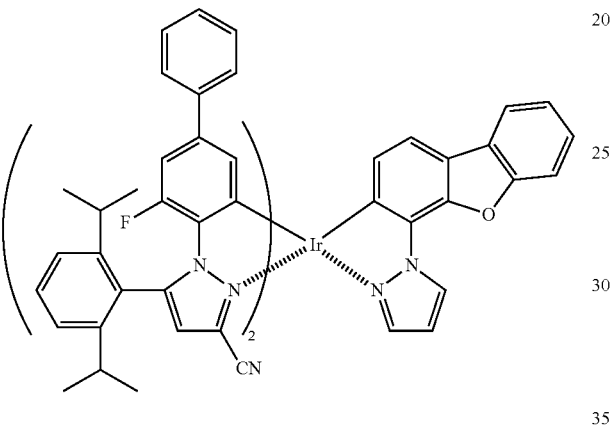
Compound 85
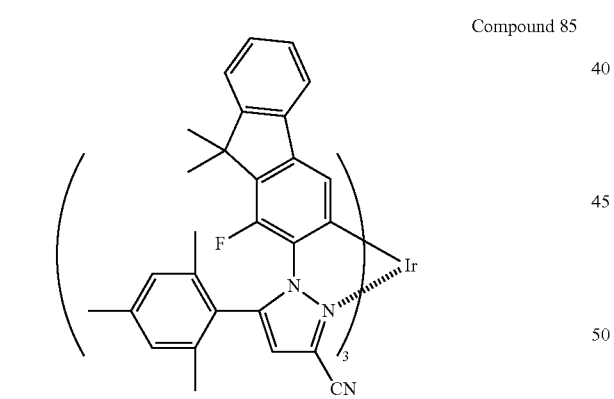
[Chemical Formula 14]
Compound 101
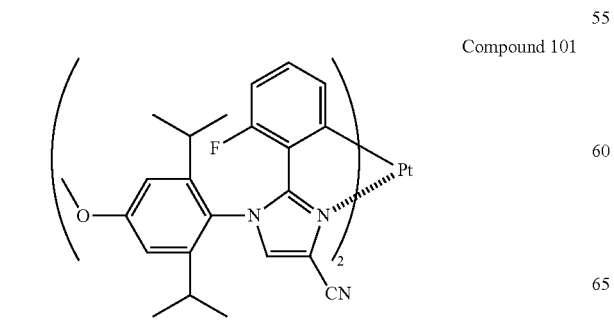
Compound 102
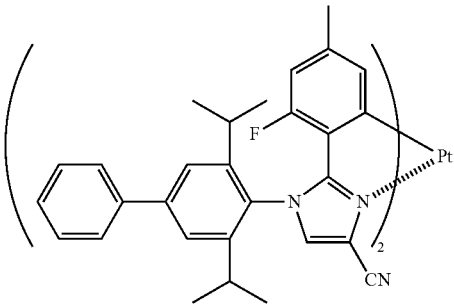
Compound 103
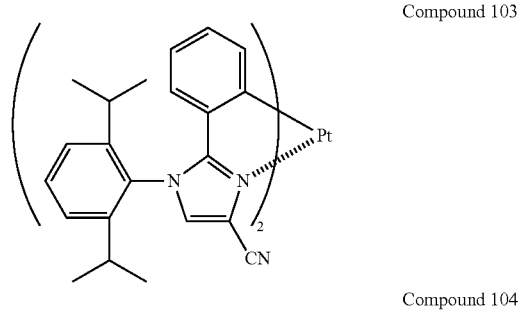
Compound 104
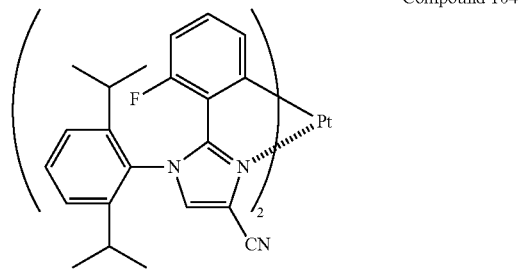
Compound 105
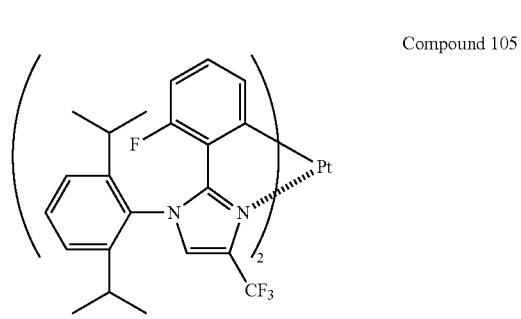
Compound 106
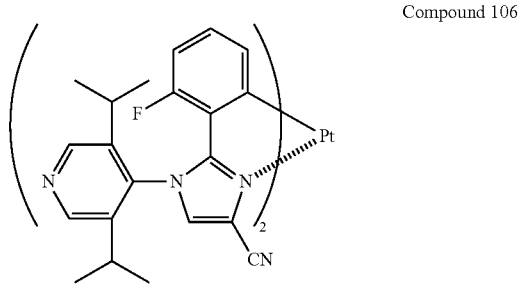

-continued
Compound 107
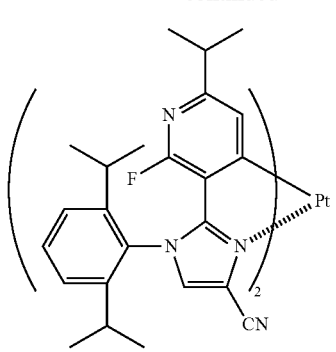
Compound 108
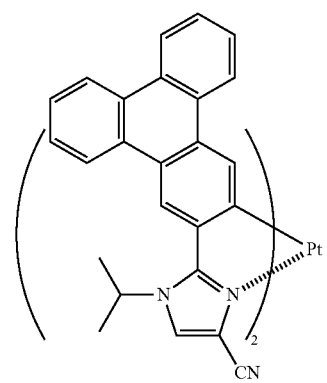
Compound 109
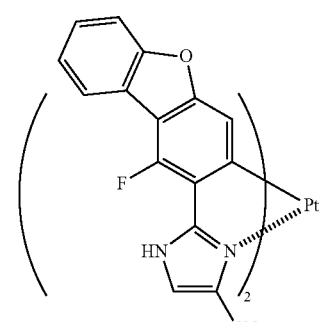
Compound 110
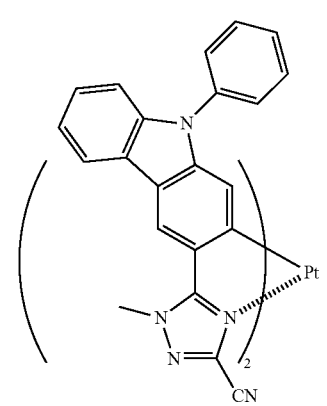
-continued
[Chemical Formula 15]
Compound 111
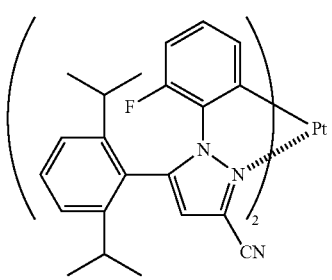
Compound 112
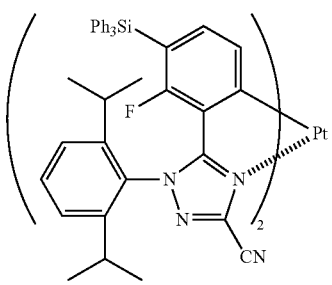
Compound 113
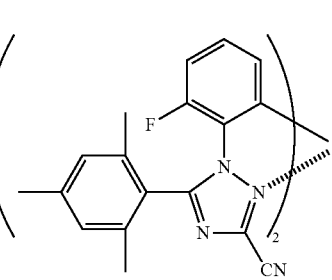
Compound 114
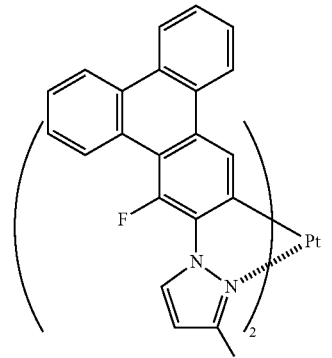
Compound 115
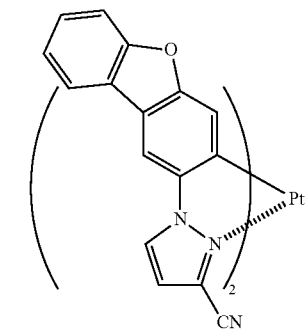

Compound 116
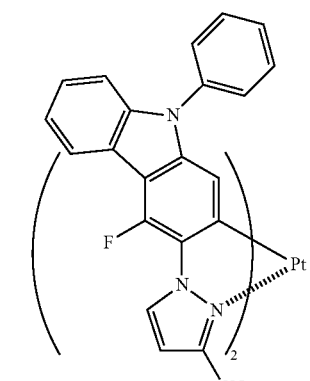
Compound 117
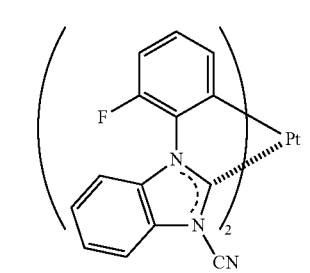
Compound 118
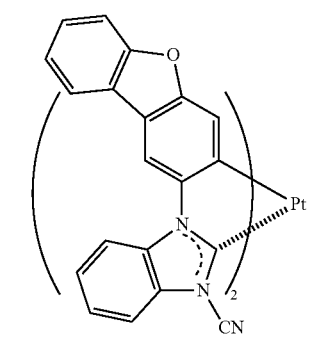
Compound 119
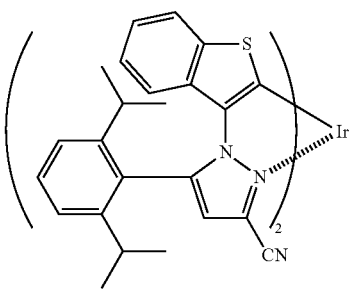
[Chemical Formula 16]
Compound 201
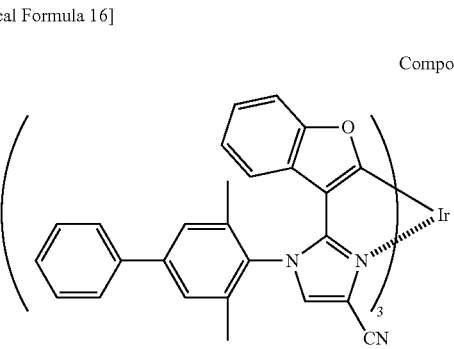
Compound 202
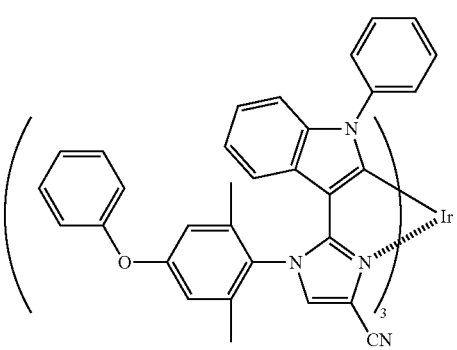
Compound 203
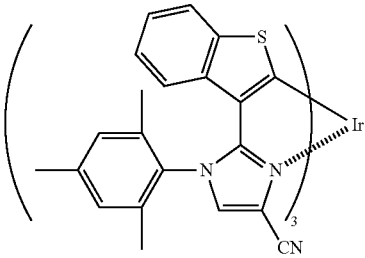
Compound 204
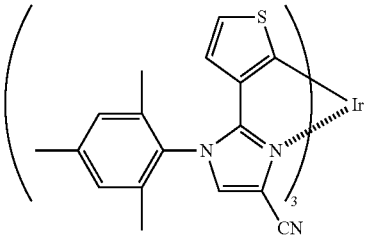
Compound 205
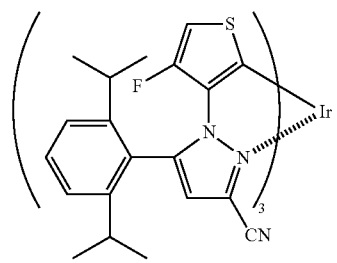
Compound 206
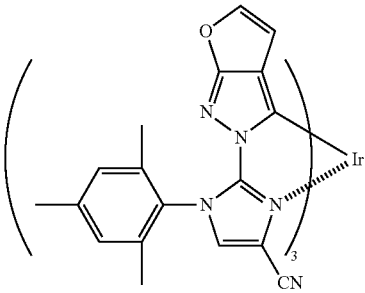

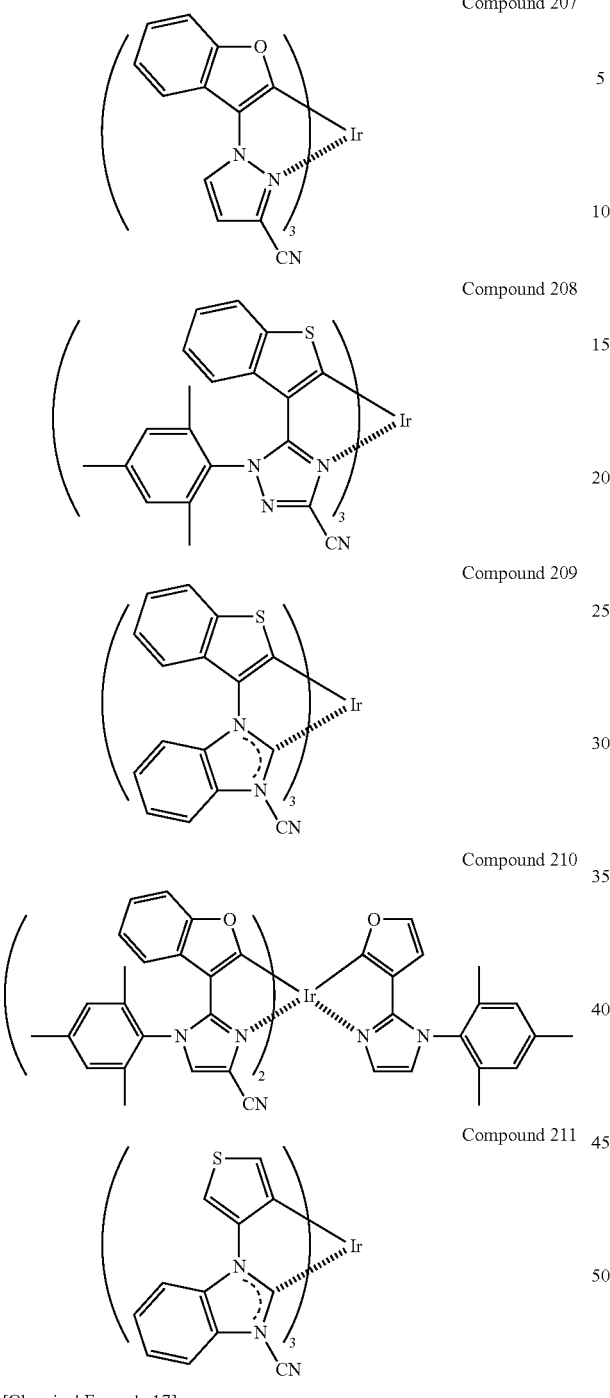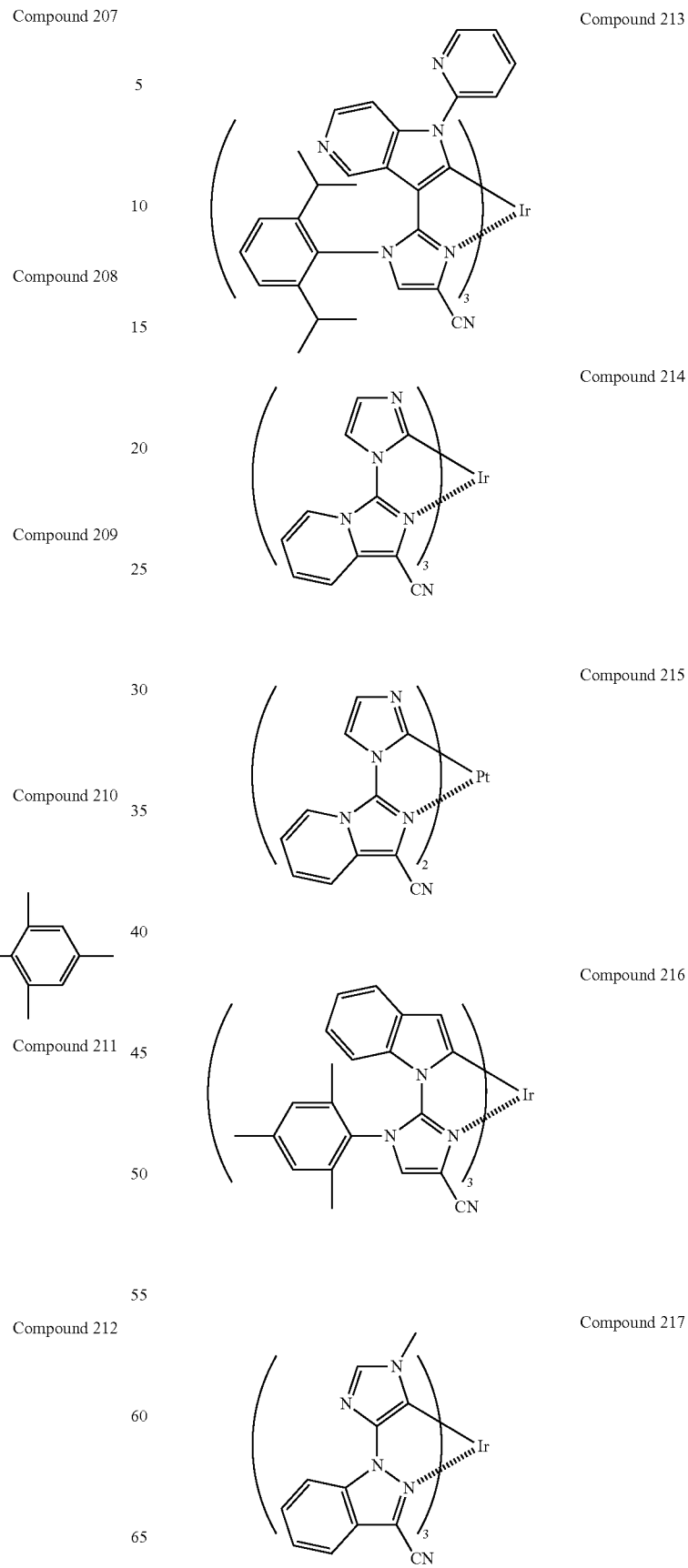

-continued
Compound 218
Compound 219
Compound 220
Compound 221
Compound 222
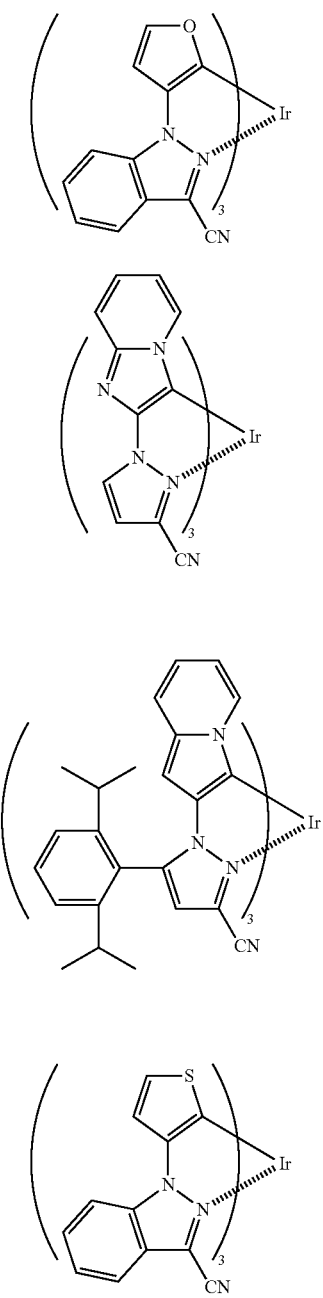
-continued
Compound 223
Compound 224
[Chemical Formula 18]
Compound 225
Compound 226
Compound 227
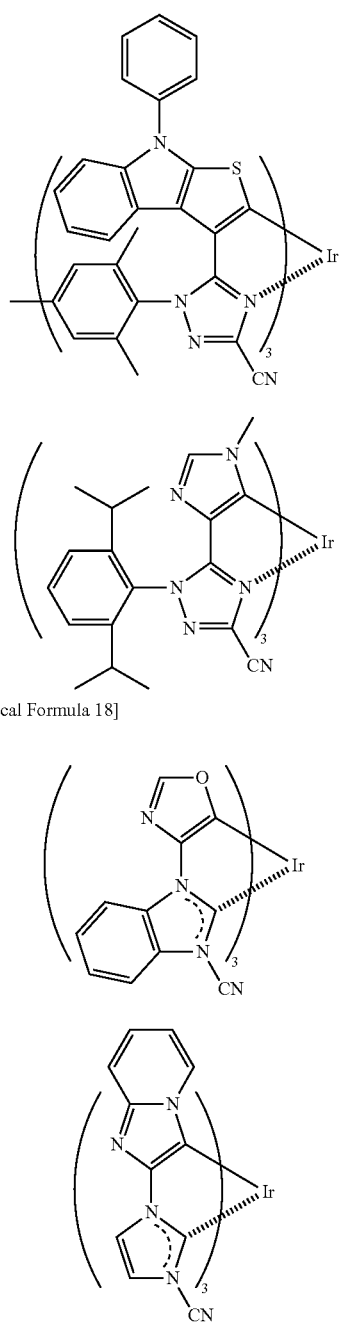

-continued

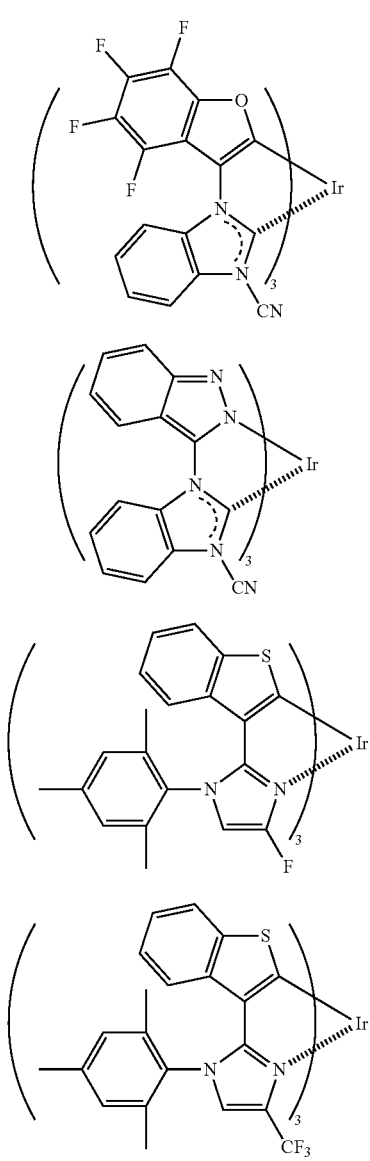

Compound 228

Compound 229

Compound 230

Compound 231

These metal complexes can be synthesized by applying the methods described in, for example, the Journal of Organic Letter, Vol. 13, No. 16, p. 2579 to 2581 (2001), Inorganic Chemistry, Vol. 30, No. 8, p. 1685 to 1687 (1991), J. Am. Chem. Soc., Vol. 123, p. 4304 (2001), Inorganic Chemistry, Vol. 40, No. 7, p. 1704 to 1711 (2001), Inorganic Chemistry, Vol. 41, No. 12, p. 3055 to 3066 (2002), New Journal of Chemistry, Vol. 26, p. 1171 (2002), Angewandte Chemie International Edition, Vol. 38, p. 1698 to 1712 (1999), Bulletin of the Chemical Society of Japan, No. 71, p. 467 to 473 (1998), J. Am. Chem. Soc., Vol. 125, No. 18, p. 5274 to 5275 (2003), J. Am. Chem. Soc., Vol. 125, No. 35, p. 10580 to 10585 (2003), and further, the reference literatures described in these literatures.

A synthesis example of the metal complex according to the present invention is presented below, but the present invention is not limited thereto.

(Synthesis of Compound 9)

In 40 ml of ethylene glycol, 1.0 g (2.7 mmol) of iridium acetate and 3.9 g (13.5 mmol) of an intermediate 1 were stirred in a nitrogen atmosphere for 3 hours while heating at 150° C. The reaction mixture was cooled to room temperature and extracted with ethyl acetate. The organic layer was washed with water, and the concentrate obtained by distilling off the solvent under reduced pressure was purified by silica gel column chromatography, thereby obtaining 0.05 g of Compound 9 exemplified.

[Chemical Formula 19]

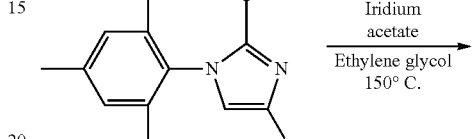

Intermediate 1

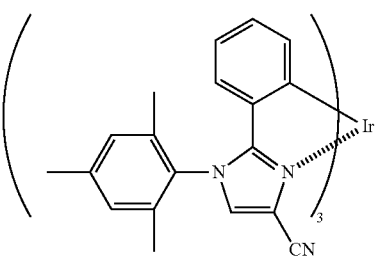

Compound 9

Incidentally, those which were further purified through the sublimation of two times were used in the fabrication of the organic EL element of the present invention to be described later.

<<Constitutional Layer of Organic EL Element>>

The constitutional layers of the organic EL element will be described. In the present invention, preferred specific examples of the layer constitution of the organic EL element are presented below, but the present invention is not limited thereto.

(i) Positive electrode/luminous layer/electron transport layer/negative electrode (ii) Positive electrode/hole transport layer/luminous layer/electron transport layer/negative electrode (iii) Positive electrode/hole transport layer/luminous layer/hole blocking layer/electron transport layer/negative electrode (iv) Positive electrode/hole transport layer/luminous layer/hole blocking layer/electron transport layer/negative electrode buffer layer/negative electrode (v) Positive electrode/positive electrode buffer layer/hole transport layer/luminous layer/hole blocking layer/electron transport layer/negative electrode buffer layer/negative electrode Incidentally, it is possible to use an electron blocking layer in addition to a hole blocking layer as a blocking layer.

A nonluminescent intermediate layer may be provided between the luminous layers in the case of including a plurality of luminous layers. In addition, it is possible to stack a plurality of luminous units by adopting the organic layers which includes a luminous layer but excludes the positive electrode and the negative electrode in the above layer constitution as one luminous unit. In the plurality of stacked luminous units, a nonluminescent intermediate layer may be provided between the luminous units, and further the intermediate layer may include a charge generating layer.

The luminous layer of the organic EL element of the present invention is preferably a white luminous layer, and the organic EL element of the present invention is preferably a lighting device or display device using this. In other words, it is preferable that the organic EL element emits light in white.

Specifically, it is preferable that the organic EL element of the present invention contains at least one luminescent dopant exhibiting a luminous color different from the luminous color of the phosphorescent organometallic complex in addition to the phosphorescent organometallic complex represented by Formula (1) above according to the present invention and emits light in white.

As the luminescent material contained in the white luminous layer, it is preferable to concurrently use a luminescent dopant exhibiting a plurality of luminous colors, and a combination of such a plurality of luminous colors may be two luminescent dopants having different maximum luminescent wavelengths, or three or more luminescent dopants having different maximum luminescent wavelengths of the three primary colors such as red, green, and blue may be combined.

Those having layers exhibiting luminescence in green and red in addition to a blue luminous layer is preferable from the viewpoint of emitting light in white with high color rendering properties and also of being easy to adjust the chromaticity in a wider range.

The respective layers constituting the organic EL element of the present invention will be described.

<<Hole Transport Layer>>

The hole transport layer is composed of a hole transporting material which has a function of transporting a hole, and a hole injection layer and an electron blocking layer are also included in the hole transport layer in a broad sense. The hole transport layer can be provided as a single layer or plural layers.

The hole transporting material are those which exhibit either of hole injection or transport properties or electron barrier properties and may be either of an organic substance or an inorganic substance. Examples thereof may include a triazole derivative, an oxadiazole derivative, an imidazole derivative, a polyarylalkane derivative, a pyrazoline derivative and a pyrazolone derivative, a phenylenediamine derivative, an arylamine derivative, an amino-substituted chalcone derivative, an oxazole derivative, a styryl-anthracene derivative, a fluorenone derivative, a hydrazone derivative, a stilbene derivative, a silazane derivative, an aniline-based copolymer, and an electroconductive macromolecular oligomer, and particularly a thiophene oligomer.

In addition, an azatriphenylene derivative as described in JP 2003-519432 W or JP 2006-135145 A can also be used as a hole transporting material in the same manner.

It is possible to use those described above as the hole transporting material, but it is preferable to use a porphyrin compound, an aromatic tertiary amine compound, and a styrylamine compound, and particularly an aromatic tertiary amine compound.

Representative examples of the aromatic tertiary amine compound and the styrylamine compound may include N,N,N',N'-tetraphenyl-4,4'-diaminophenyl; N,N'-diphenyl-N,N'-bis(3-methylphenyl)-[1,1'-biphenyl]-4,4'-diamine (TPD); 2,2-bis(4-di-p-tolylaminophenyl)propane; 1,1-bis(4-di-p-tolylaminophenyl)cyclohexane; N,N,N',N'-tetra-p-tolyl-4,4'-diaminobiphenyl; 1,1-bis(4-di-p-tolylaminophenyl)-4-phenylcyclohexane; bis(4-dimethylamino-2-methylphenyl)phenylmethane; bis(4-di-p-tolylaminophenyl)phenylmethane; N,N'-diphenyl-N,N'-di(4-methoxyphenyl)-4,4'-diaminobiphenyl; N,N,N',N'-tetraphenyl-4,4'-diaminodiphenyl ether; 4,4'-bis(diphenylamino) quadriphenyl; N,N,N-tri(p-tolyl)amine; 4-(di-p-tolylamino)-4'-[4-(di-p-tolylamino) styryl]stilbene; 4-N,N-diphenylamino-(2-diphenylvinyl)benzene; 3-methoxy-4'-N,N-diphenylaminostilbene; N-phenylcarbazole, further, those that have two condensed aromatic rings in the molecule and are described in U.S. Pat. No. 5,061,569, for example, 4,4'-bis[N-(1-naphthyl)-N-phenylamino]biphenyl (NPD), and 4,4',4"-tris[N-(3-methylphenyl)-N-phenylamino]triphenylamine (MTDATA) that is described in JP 4-308688 A and has a structure in which three triphenylamine units are coupled in a starburst shape.

Furthermore, it is also possible to use a polymer material obtained by introducing these materials into the polymer chain or a polymer material obtained by using these materials as the main chain of the polymer.

In addition, it is also possible to use an inorganic compound such as p-type Si or p-type SiC as the hole injecting material and the hole transporting material.

In addition, it is also possible to use a so-called p-type hole transporting material as described in JP 11-251067 A and a literature (Applied Physics Letters 80 (2002), p. 139) written by J. Huang et. al. In the present invention, it is preferable to use these materials since a luminescent element having a higher efficiency is obtained.

The hole transport layer can be formed by thinning the hole transporting material into a film by a known method, for example, a vacuum deposition method, a spin coating method, a casting method, or a printing method including an ink-jet method, or a LB method.

The thickness of the hole transport layer is not particularly limited, but it is usually about in a range of from 5 nm to 5 µm and preferably in a range of from 5 to 200 nm. This hole transport layer may have a single layer structure composed of one kind or two or more kinds of the above materials.

In addition, it is also possible to use a hole transport layer that is doped with impurities and exhibits high p-properties. Examples thereof may include those described in JP 4-297076 A, JP 2000-196140 A, JP 2001-102175 A, J. Appl. Phys. 95, 5773 (2004), and the like.

In the present invention, it is preferable to use such a hole transport layer exhibiting high p-type properties since an element having lower power consumption can be fabricated.

<<Electron Transport Layer>>

The electron transport layer is composed of a material which has a function of transporting an electron, and an electron injection layer and a hole blocking layer are also included in the electron transport layer in a broad sense. The electron transport layer can be provided as a single layer or plural layers.

The electron transport layer is only desired to have a function of transporting an electron injected from the negative electrode to the luminous layer, and it is also possible to select an arbitrary compound from the compounds known in the prior art and to concurrently use it as a material for the electron transport layer.

Examples of the material (hereinafter, referred to as the electron transporting material) that is used for the electron transport layer and known in the prior art may include a nitro-substituted fluorene derivative, a diphenylquinone derivative, a thiopyrandioxide derivative, a polycyclic aromatic hydrocarbon such as naphthalene or perylene, a heterocyclic tetracarboxylic anhydride, carbodiimide, a fluorenylidenemethane derivative, anthraquinodimethane and anthrone derivatives, an oxadiazole derivative, a carboline derivative, or a derivative having a ring structure in which at least one of the carbon atoms of the hydrocarbon ring constituting the carboline ring of the carboline derivative is substituted with a nitrogen atom, and a hexaazatriphenylene derivative.

Furthermore, it is also possible to use a thiadiazole derivative obtained by substituting an oxygen atom in the oxadiazole ring in the above-mentioned oxadiazole derivative with a sulfur atom and a quinoxaline derivative having a quinoxaline ring known as an electron withdrawing group as the electron transporting material.

It is also possible to use a polymer material obtained by introducing these materials into the polymer chain or a polymer material obtained by using these materials as the main chain of the polymer.

In addition, it is also possible to use a metal complex of a 8-quinolinol derivative, for example, tris(8-quinolinol) aluminum (Alq), tris(5,7-dichloro-8-quinolinol)aluminum, tris(5,7-dibromo-8-quinolinol)aluminum, tris(2-methyl-8-quinolinol)aluminum, tris(5-methyl-8-quinolinol)aluminum, or bis(8-quinolinol)zinc (Znq) and a metal complex obtained by substituting the central metal of these metal complexes with In, Mg, Cu, Ca, Sn, Ga or Pb as the electron transporting material.

In addition to these, it is also possible to use metal-free or metal phthalocyanine or those obtained by substituting the end of them with an alkyl group or a sulfonic acid group as the electron transporting material. In addition, it is also possible to use an inorganic semiconductor such as n-type Si or n-type SiC as the electron transporting material.

The electron transport layer can be formed by thinning the electron transporting material into a film, for example, by a vacuum deposition method or a wet method (also referred to as the wet process, examples thereof may include a spin coating method, a casting method, a die coating method, a blade coating method, a roll coating method, an ink-jet method, a printing method, a spray coating method, a curtain coating method, and a LB method (Langmuir Blodgett method)).

The thickness of the electron transport layer is not particularly limited, but it is usually about in a range of from 5 to 5000 nm and preferably in a range of from 5 to 200 nm. This electron transport layer may have a single layer structure composed of one kind or two or more kinds of the above materials.

In addition, the electron transport layer may be used by doping a n-type dopant such as a metal complex or a metal compound such as a metal halide.

Examples of the compound (electron transporting material) that is preferably used to form the electron transport layer of the organic EL element of the present invention may include Compounds ET-1 to ET-43 described in JP 2012-164731A, but it is not limited thereto.

<<Luminous Layer>>

The organic EL element of the present invention has at least one luminous layer sandwiched between the positive electrode and the negative electrode and contains at least one kind of phosphorescent organometallic complex having a structure represented by Formula (1) above in the luminous layer.

The luminous layer is a layer in which the electron and the hole that are injected from the electrode or the electron transport layer and the hole transport layer are rebound to emit light, and the part at which light emits may be in the luminous layer or at the interface between the luminous layer and the adjacent layer.

The sum of the thicknesses of the luminous layers is not particularly limited, but it is preferably adjusted to be in a range of from 2 nm to 5 µm, and it is even more preferably adjusted to be in a range of from 2 to 200 nm, and it is particularly preferably adjusted to be in a range of from 5 to 100 nm from the viewpoint of uniformity of the films or the prevention of application of an unrequired high voltage at the time of emitting light and the improvement in stability of the luminous color with respect to the driving current.

For the fabrication of the luminous layer, the luminous layer can be formed by forming a film using a luminescent dopant or host compound to be described below, for example, by a vacuum deposition method or a wet method (also referred to as the wet process, examples thereof may include a spin coating method, a casting method, a die coating method, a blade coating method, a roll coating method, an ink-jet method, a printing method, a spray coating method, a curtain coating method, and a LB method (Langmuir Blodgett method)). Incidentally, it is preferable to form a film by a wet process when using a phosphorescent organometallic complex used in the present invention as a material for the luminous layer.

The luminous layer of the organic EL element of the present invention contains at least one kind of phosphorescent organometallic complex represented by Formula (1) described above as a phosphorescent dopant. In addition, it is preferable that the luminous layer contains a host compound.

(Luminescent Dopant)

The luminescent dopant will be described. As the luminescent dopant, at least one kind of phosphorescent organometallic complex (a kind of phosphorescent dopant) according to the present invention is used.

As a luminescent dopant which may be concurrently used with the phosphorescent organometallic complex, it is possible to use a fluorescent dopant and a phosphorescent dopant other than the phosphorescent organometallic complex.

(Phosphorescent Dopant)

The phosphorescent dopant is a compound from which luminescence from the excited triplet state is observed, and specifically it is a compound which exhibits phosphorescence at room temperature (25° C.) and it is defined as a compound which has a phosphorescence quantum yield of 0.01 or more at 25° C., but a preferred phosphorescence quantum yield is 0.1 or more.

The phosphorescence quantum yield can be measured by the method described in the Experimental Chemistry 7, Fourth Edition, Spectroscopy II, page 398 (1992, published by Maruzen). The phosphorescence quantum yield in a solution can be measured using various solvents, but the phosphorescent dopant according to the present invention is only desired to achieve the phosphorescence quantum yield (0.01 or more) described above in any one of arbitrary solvents.

The luminescence by the phosphorescent dopant is divided into two types in principle, and one is an energy transfer type in which the recombination of carriers occurs on the host compound to which the carrier is transported so as to generate the excited state of the host compound, and luminescence from the phosphorescent dopant is obtained by transferring this energy to the phosphorescent dopant. The other one is a carrier trap type in which the phosphorescent dopant is a carrier trap and the recombination of carriers occurs on the phosphorescent dopant so as to obtain luminescence from the phosphorescent dopant. In either case, it is a condition that the energy of the phosphorescent dopant in the excited state is lower than the energy of the host compound in the excited state.

In addition, the compounds described in the patent publications below and the like may be concurrently used in the luminous layer.

Examples thereof may include the compounds described in WO 00/70655 A, JP 2002-280178 A, JP 2001-181616 A, JP 2002-280179 A, JP 2001-181617 A, JP 2002-280180 A, JP 2001-247859 A, JP 2002-299060 A, JP 2001-313178 A, JP 2002-302671 A, JP 2001-345183 A, JP 2002-324679 A, WO 02/15645 A, JP 2002-332291 A, JP 2002-50484 A, JP-2002-332292 A, JP-2002-83684 A, JP 2002-540572 W, JP 2002-117978 A, JP 2002-338588 A, JP 2002-170684 A, JP 2002-352960 A, WO 01/93642 A, JP 2002-50483 A, JP 2002-100476 A, JP 2002-173674 A, JP 2002-359082 A, JP 2002-175884 A, JP 2002-363552 A, JP 2002-184582 A, JP 2003-7469 A, JP 2002-525808 W, JP 2003-7471 A, JP 2002-525833 W, JP 2003-31366 A, JP 2002-226495 A, JP 2002-234894 A, JP 2002-235076 A, JP 2002-241751 A, JP 2001-319779A, JP 2001-319780 A, JP 2002-62824 A, JP 2002-100474 A, JP 2002-203679 A, JP 2002-343572 A, JP 2002-203678 A, and the like.

(Fluorescent Dopant)

Examples of the fluorescent dopant may include a coumarin-based coloring matter, a pyran-based coloring matter, a cyanine-based coloring matter, a croconium-based coloring matter, a squarylium-based coloring matter, an oxobenzanthracene-based coloring matter, a fluorescein-based coloring matter, a rhodamine-based coloring matter, a pyrylium-based coloring matter, a perylene-based coloring matter, a stilbene-based coloring matter, a polythiophene-based coloring matter, or a rare earth complex-based fluorophore, or compound which has a high fluorescent quantum yield and is represented by a laser coloring matter.

In the present invention, plural kinds of compounds may be concurrently used as the luminous dopant in a range in which the effect is not affected, and a combination of phosphorescent dopants having different structures or combination of a phosphorescent dopant and a fluorescent dopant may be used.

Incidentally, specific examples of the preferred known phosphorescent dopant compound that can be concurrently used with the phosphorescent organometallic complex according to the present invention may include Compounds D-1 to D-47 described in JP 2012-195554 A, but it is not limited thereto.

(Host Compound)

The host compound that can be used in the present invention is not particularly limited, and it is possible to use the compounds that are used in the organic EL element of the prior art.

Examples of the compound known in the prior art may representatively include a carbazole derivative, a triarylamine derivative, an aromatic derivative, a nitrogen-containing heterocyclic compound, a thiophene derivative, a furan derivative, those having a basic backbone such as an oligoarylene compound, or a carboline derivative or a diazacarbazole derivative (here, the diazacarbazole derivative represents those that are obtained by substituting at least one carbon atom of the hydrocarbon ring which constitutes the carboline ring of a carboline derivative with a nitrogen atom).

Specific examples of the known host compound may include the compounds described in the following literatures.

JP 2001-257076 A, JP 2002-308855 A, JP 2001-313179 A, JP 2002-319491 A, JP 2001-357977 A, JP 2002-334786 A, JP 2002-8860 A, JP 2002-334787 A, JP 2002-15871 A, JP 2002-334788 A, JP 2002-43056 A, JP 2002-334789 A, JP 2002-75645 A, JP 2002-338579 A, JP 2002-105445 A, JP 2002-343568 A, JP 2002-141173 A, JP 2002-352957 A, JP 2002-203683 A, JP 2002-363227 A, JP 2002-231453 A, JP 2003-3165 A, JP 2002-234888 A, JP 2003-27048 A, JP 2002-255934 A, JP 2002-260861 A, JP 2002-280183 A, JP 2002-299060 A, JP 2002-302516 A, JP 2002-305083 A, JP 2002-305084 A, JP 2002-308837 A, and the like.

Incidentally, specific examples to be used as a known host compound for the luminous layer of the organic EL element of the present invention may include Compounds OC-1 to OC-32 described in JP 2012-164731 A, but it is not limited thereto.

Furthermore, particularly preferred examples as the host compound for the luminous layer of the organic EL element of the present invention may include Compounds 1 to 56 that are the compounds represented by Formula (B) described in JP 2012-164731 A, but it is not limited thereto.

<<Injection Layer: Hole Injection Layer (Positive Electrode Buffer Layer) and Electron Injection Layer (Negative Electrode Buffer Layer)>>

The injection layer refers to a layer that is provided between the electrode and the organic layer in order to lower the driving voltage or to improve the luminescent brightness if necessary, it is described in detail in the "Organic EL Element and its Industrialization Front (Nov. 30, 1998 published by (C) NTS, Inc.)", Part II, Chapter 2 "Electrode Material" (pp. 123-166), and there are a hole injection layer (positive electrode buffer layer) and an electron injection layer (negative electrode buffer layer).

The positive electrode buffer layer (hole injection layer) is also described in detail in JP 9-45479 A, JP 9-260062 A, JP 8-288069 A, and the like, and specific examples thereof may include a phthalocyanine buffer layer represented by copper phthalocyanine, a hexaazatriphenylene derivative buffer layer as described in JP 2003-519432 W, JP 2006-135145 A, and the like, an oxide buffer layer represented by vanadium oxide, an amorphous carbon buffer layer, a polymer buffer layer using a conductive polymer such as polyaniline (emeraldine) or polythiophene, and an ortho-metalated complex layer represented by tris(2-phenylpyridine) iridium complex.

The negative electrode buffer layer (electron injection layer) is also described in detail in JP 6-325871 A, JP 9-17574 A, JP 10-74586 A, and the like, and specific examples thereof may include a buffer layer of a metal represented by strontium or aluminum, a buffer layer of an alkali metal compound represented by lithium fluoride or potassium fluoride, a buffer layer of an alkaline earth metal compound represented by magnesium fluoride or cesium fluoride, and a buffer layer of an oxide represented by aluminum oxide. It is desirable that the above-described buffer layer (injection layer) is a significantly thin film, and the thickness is preferably in a range of 0.1 nm to 5 μm although it also depends on the material.

<<Blocking Layer: Hole Blocking Layer and Electron Blocking Layer>>

The blocking layer is one that is provided if necessary in addition to the basic constitutional layers of the organic compound thin film as described above. For example, there is a hole blocking layer described in JP 11-204258 A, JP 11-204359 A, and the "Organic EL Element and its Industrialization Front (Nov. 30, 1998 published by (C) NTS, Inc.)", p. 237.

The hole blocking layer has the function of an electron transport layer in a broad sense and it is composed of a hole blocking material which has significantly small ability of transporting a hole while having a function of transporting an electron, and it is possible to increase the probability of recombination of an electron with a hole by blocking a hole while transporting an electron.

In addition, it is possible to use the constitution of the electron transport layer to be described later as the hole blocking layer according to the present invention if necessary.

It is preferable that the hole blocking layer of the organic EL element of the present invention is provided so as to be adjacent to the luminous layer.

It is preferable that the hole blocking layer contains a carbazole derivative, a carboline derivative, and a diazacarbazole derivative (here, the diazacarbazole derivative represents one that is obtained by substituting at least one of the carbon atoms constituting a carboline ring with a nitrogen atom) exemplified as the host compound described above.

In addition, in the present invention, it is preferable that the luminous layer (shortest wavelength layer) having the shortest maximum luminescent wavelength is closest to the positive electrode among the luminous layers in the case of having a plurality of luminous layers having a plurality of different luminous colors. Moreover, in such a case, it is preferable to additionally provide a hole blocking layer between the shortest wavelength layer and the luminous layer that is closer to the positive electrode after the shortest wavelength layer.

The thickness of the hole blocking layer and the electron transport layer which can be used in the present invention is preferably in a range of from 3 to 100 nm and even more preferably in a range of from 5 to 30 nm.

<<Negative Electrode>>

Meanwhile, as the negative electrode, those are used which contain a metal (referred to as an electron injecting metal), an alloy, an electrically conductive compound, and a mixture thereof which have a small work function (4 eV or less) as an electrode substance. Specific examples of such an electrode substance may include sodium, a sodium-potassium alloy, magnesium, lithium, a magnesium/copper mixture, a magnesium/silver mixture, a magnesium/aluminum mixture, a magnesium/indium mixture, an aluminum/aluminum oxide ($Al_2O_3$) mixture, indium, a lithium/aluminum mixture, and a rare earth metal. Among these, a mixture of an electron injecting metal and a second metal of a metal which has a greater work function value than the electron injecting metal and is stable, for example, a magnesium/silver mixture, a magnesium/aluminum mixture, a magnesium/indium mixture, an aluminum/aluminum oxide ($Al_2O_3$) mixture, a lithium/aluminum mixture, or aluminum is suitable from the viewpoint of electron injection properties and durability against oxidation or the like.

The negative electrode can be fabricated by forming these electrode substances into a thin film by a method such as vapor deposition or sputtering. In addition, the sheet resistance as a negative electrode is preferably several hundred $\Omega/\square$ or less, and the thickness is selected in a range of usually from 10 nm to 5 μm and preferably from 50 to 200 nm. Incidentally, it is favorable that either of the positive electrode or negative electrode of the organic EL element is transparent or translucent in order to transmit the emitted light since the luminescent brightness is improved.

In addition, it is possible to fabricate a transparent or translucent negative electrode by fabricating a film of the metal on the negative electrode in a thickness range of from 1 to 20 nm and then fabricating a film of the conductive transparent material to be exemplified later in the description of the positive electrode thereon, and it is possible to fabricate an element in which both the positive electrode and the negative electrode exhibit transparency by applying this.

<<Positive Electrode>>

As the positive electrode of the organic EL element, those are preferably used which contain a metal, an alloy, an electrically conductive compound, and a mixture thereof which have a great work function (4 eV or more) as an electrode substance. Specific examples of such an electrode substance may include a metal such as Au and a conductive transparent material such as CuI, indium tin oxide (ITO), $SnO_2$, or ZnO.

In addition, a material that is amorphous and able to be fabricated into a transparent conductive film such as IDIXO ($In_2O_3$—ZnO) may be used. As the positive electrode, these electrode substances are formed into a thin film by a method such as vapor deposition or sputtering, and a pattern having a desired shape may be formed by photolithography or a pattern may be formed via a mask having a desired shape at the time of vapor deposition or sputtering of the electrode substance in a case in which the accuracy of pattern is not much required (about 100 μm or more).

Alternatively, it is also possible to use a wet film forming method such as a printing method or a coating method in the case of using a coatable substance such as an organic conductive compound. It is desirable to set the transmittance to be greater than 10% in the case of extracting the luminescence through this positive electrode, and the sheet resistance as a positive electrode is preferably several hundred $\Omega/\square$ or less. Furthermore, the thickness is selected usually in a range of from 10 to 1000 nm and preferably in a range of from 10 to 200 nm although it also depends on the material.

<<Substrate>>

As the substrate (hereinafter, also referred to as the supporting substrate, the substrate, the support, or the like) which can be used in the organic EL element of the present invention, the kind of the glass, plastic, or the like is not particularly limited, and it may be transparent or opaque. It is preferable that the substrate is transparent in the case of extracting the light from the substrate side. Examples of the preferably usable transparent substrate may include glass, quartz, and a transparent resin film. A particularly preferred substrate is a resin film capable of imparting flexibility to the organic EL element.

<<Method for Fabricating Organic EL Element>>

The method for fabricating an element which consists of positive electrode/hole injection layer (positive electrode buffer layer)/hole transport layer/luminous layer/hole blocking layer/electron transport layer/electron injection layer (negative electrode buffer layer)/negative electrode will be described as an example of the method for fabricating the organic EL element.

First, a thin film composed of a desired electrode substance, for example, a substance for positive electrode is formed on a proper substrate so as to have a thickness of 1 μm or less and preferably in a range of from 10 to 200 nm, thereby fabricating the positive electrode.

Next, thin films containing organic compounds of element materials such as the hole injection layer, the hole transport layer, the luminous layer, the hole blocking layer, the electron transport layer, and the electron injection layer are formed thereon.

As the method for forming the thin film, for example, the thin film can be formed by a vacuum deposition method, a wet method (also referred to as the wet process), or the like. However, in the present invention, it is preferable to fabricate the organic EL element by the wet process. It is possible to exhibit an effect of being likely to obtain a uniform film, of hardly generating pin holes, or the like as the organic EL element is fabricated by the wet process.

There are a spin coating method, a casting method, a die coating method, a blade coating method, a roll coating method, an ink-jet method, a printing method, a spray coating method, a curtain coating method, and a LB method, and the like as the wet method, but a method that is highly suitable for the roll-to-roll method, such as a die coating method, a roll coating method, an ink-jet method, or a spray coating method is preferable from the viewpoint of being able to form a precise thin film and having high productivity. In addition, different film forming methods may be applied for each layer.

As a liquid medium for dissolving or dispersing the organic EL materials which can be used in the present invention, it is possible to use, for example, a ketone such as methyl ethyl ketone or cyclohexanone, a fatty acid ester such as ethyl acetate, a halogenated hydrocarbon such as dichlorobenzene, an aromatic hydrocarbon such as toluene, xylene, mesitylene, or cyclohexylbenzene, an aliphatic hydrocarbon such as cyclohexane, decalin, or dodecane, and an organic solvent such as DMF or DMSO.

In addition, as the dispersing method, it is possible to disperse the materials by ultrasonic waves and a dispersing method such as high shear dispersion or media dispersion.

After these layers are formed, a thin film composed of a substance for negative electrode is formed thereon so as to have a thickness of 1 µm or less and preferably in a range of from 50 to 200 nm to provide the negative electrode, whereby a desired organic EL element is obtained.

In addition, it is also possible to reverse the order of fabrication so as to fabricate the negative electrode, the electron injection layer, the electron transport layer, the hole blocking layer, the luminous layer, the hole transport layer, the hole injection layer, and the positive electrode in this order.

For the fabrication of the organic EL element of the present invention, it is preferable to consistently fabricate from the hole injection layer to the negative electrode by vacuum drawing of one time, but the substrate may be taken out in the middle of the fabrication so as to be subjected to a different film forming method. In that case, it is preferable to conduct the operation in a dry inert gas atmosphere.

<<Sealing>>

Examples of the sealing means used in the present invention may include a method in which the sealing member is pasted to the electrode and the substrate using an adhesive.

The sealing member is only desired to be disposed so as to cover the display region of the organic EL element, and it may have a recessed plate shape or a flat plate shape. In addition, the transparency and electrical insulating properties thereof are not particularly limited. Specific examples thereof may include a glass plate, a polymer plate or film, and a metal plate or film.

A sand blasting process, a chemical etching process, or the like is used in order to process the sealing member into a recessed shape.

In addition, it can be also suitable to form a layer of an inorganic substance or an organic substance in the form of covering the electrode and the organic layer on the outside of the electrode on the side to sandwich the organic layer and to face the substrate and of being in contact with the substrate and to adopt the layer as the sealing film.

<<Protective Film and Protective Plate>>

The outside of the sealing film or the film for sealing on the side to sandwich the organic layer and to face the substrate may be provided with a protective film or a protective plate in order to enhance the mechanical strength of the element. The mechanical strength is not always high particularly in a case in which the sealing is conducted using the sealing film, and thus it is preferable to provide such a protective film or protective plate. As the material which can be used for this, it is possible to use a glass plate, a polymer plate or film, and a metal plate or film which are the same as those used in the sealing, but it is preferable to use a polymer film from the viewpoint of light weight and thinning.

<<Light Extraction>>

An organic EL element is generally said that light is emitted inside of a layer which has a higher refractive index (refractive index in a range of about from 1.7 to 2.1) than the air and only light to be about from 15 to 20% of the light generated in the luminous layer is extracted. This is because the light incident on the interface (interface between the transparent substrate and the air) at an angle $\theta$ to be equal to or higher than the critical angle cannot be extracted to the outside of the element due to the total reflection or the total reflection of light is caused between the transparent electrode or the luminous layer and the transparent substrate so that the light is guided through the transparent electrode or the luminous layer and, as a result, the light escapes in the side direction of the element.

Examples of the method for improving the this light extraction efficiency may include a method in which a concave and a convex are formed on the transparent substrate surface to prevent the total reflection at the interface between the transparent substrate and the air (for example, U.S. Pat. No. 4,774,435), a method in which light collecting properties are imparted to the substrate to improve the efficiency (for example, JP 63-314795 A), a method in which a reflective surface is formed on the side surface or the like of the element (for example, JP 1-220394 A), a method in which a flat layer having an intermediate refractive index is introduced between the substrate and the luminous body to form an antireflective film (for example, JP 62-172691 A), a method in which a flat layer having a refractive index lower than that of the substrate is introduced between the substrate and the luminous body (for example, JP 2001-202827 A), and a method in which a diffraction grating is formed between the substrate and either layer of the transparent electrode layer or the luminous layer (including, between the substrate and the outside) (JP 11-283751 A).

In the present invention, it is possible to use these methods in combination with the organic EL element of the present invention, but it is possible to suitably use a method in which a flat layer having a refractive index lower than that of the substrate is introduced between the substrate and the luminous body or a method in which a diffraction grating is formed between the substrate and either of the transparent electrode layer or the luminous layer (including, between the substrate and the outside).

In the present invention, it is possible to obtain an element which has a higher brightness or exhibits excellent durability by combining these means.

<<Light Collecting Sheet>>

It is possible to enhance the brightness in a specific direction as light is collected in a specific direction, for example, the front direction with respect to the luminous surface of the element by processing the organic EL element of the present invention so as to provide, for example, a microlens-arrayed structure on the light extracting side of the substrate or combining with the so-called light collecting sheet.

As an example of the microlens array, a quadrangular pyramid of which one side is 30 μm and the apex angle is 90 degrees is two-dimensionally arranged on the light extracting side of the substrate. One side is preferably in a range of from 10 to 100 μm. It is not preferable that one side is smaller than this since the effect of diffraction is generated and coloring is caused and it is also not preferable that one side is greater than this since the thickness increases.

Incidentally, the details other than the characteristic parts of the present invention on the "respective layers constituting organic EL element" described above or the other details on the "substrate", "sealing", "protective film and protective plate", "light extraction", "light collecting sheet" and the like are the same as those described in known literatures, for example, JP 2012-164731 A and JP 2012-156299 A.

<<Applications>>

The organic EL element of the present invention can be used as a display device, a display, and a light source for various kinds of luminescence. Examples of the light source for luminescence may include a lighting device (home lighting, vehicle interior lighting), a watch or a backlight for liquid crystal, a billboard, a traffic light, a light source for an optical storage medium, a light source for an electrophotographic copying machine, a light source for an optical communication processing machine, and a light source for an optical sensor, and the application thereof is not limited thereto, but the organic EL element of the present invention can be effectively used in the application particularly as a backlight for a liquid crystal display device and a light source for lighting.

In the organic EL element of the present invention, the patterning may be conducted using a metal mask or an ink-jet printing method at the time of film formation if necessary. In the case of conducting the patterning, only the electrode may be patterned, the electrode and the luminous layer may be patterned, or all the layers of the element may be patterned, and it is possible to use a method known in the prior art in the fabrication of the element. The color of light emitted from the organic EL element of the present invention or the compound used in the present invention is determined by the color at the time of applying the results measured using a spectroradiometer CS-1000 (manufactured by Konica Minolta, Inc.) to the CIE chromaticity coordinate in FIG. 4.16 on page 108 of the "New Version Color Science Handbook" (edited by Color Science Association of Japan, University of Tokyo Press, 1985).

In addition, in a case in which the organic EL element of the present invention is an element emitting light in white, it is preferable that the white color has a chromaticity in a region of x=0.33±0.07 and y=0.33±0.1 in the CIE1931 color system at 1000 cd/m$^2$ when 2-degree viewing angle front brightness is measured by the method described above.

<<Display Device>>

The display device of the present invention will be described. The display device of the present invention is one that includes the organic EL element of the present invention. The display device of the present invention may be in a single color or multiple colors, but a multicolor display device will be described herein.

In the case of a multicolor display device, it is possible to form a film on the entire surface by a vapor deposition method, a casting method, a spin coating method, an ink-jet method, a printing method, and the like by providing the shadow mask only at the time of forming the luminous layer. In the case of patterning only the luminous layer, although the method therefor is not limited, but it is possible to preferably apply a vapor deposition method, an ink-jet method, a spin coating method, and a printing method.

The constitution of the organic EL element to be included in a display device can be selected from the constitutional examples of the organic EL element described above if necessary.

In addition, the method for manufacturing the organic EL element is as presented in an aspect of the manufacture of the organic EL element of the present invention described above.

In the case of applying a DC voltage to the multicolor display device thus obtained, it is possible to observe luminescence as the polarity of the positive electrode is set to +, the polarity of the negative electrode is set to −, and a voltage in a range of about from 2 to 40 V is applied. In addition, the electric current does not flow and luminescence does not occur at all even when a voltage is applied if the polarity is reversed. Furthermore, luminescence is observed only in a state in which the positive electrode is + and the negative electrode is − in the case of applying an AC voltage. Incidentally, the waveform of the alternating current to be applied may be arbitrary.

The multicolor display device can be used as a display device, a display, and a light source for various kinds of luminescence. In the display device and the display, it is possible to display full color by using three kinds of organic EL elements that emit light in blue, red, and green, respectively.

Examples of the display device and the display may include a television, a personal computer, mobile equipment, AV equipment, a display for text broadcasting, and an information display used in a vehicle. It may be used as a display device particularly for reproducing a still image or a moving image, and the driving system in the case of being used as a display device for reproducing a moving image may be either of a simple matrix (passive matrix) system or an active matrix system.

Examples of the light source for luminescence may include home lighting, vehicle interior lighting, a watch or a backlight for liquid crystal, a billboard, a traffic light, a light source for an optical storage medium, a light source for an electrophotographic copying machine, a light source for an optical communication processing machine, and a light source for an optical sensor, but the present invention is not limited thereto.

Hereinafter, an example of the display device having the organic EL element of the present invention will be described with reference to the drawings. FIG. 1 is a schematic view illustrating an example of the display device constituted by an organic EL element. It is a schematic view of a display for displaying the image information by luminescence from an organic EL element, for example, a mobile phone.

A display 1 consists of a display unit A having a plurality of pixels and a control unit B for scanning the image of the display unit A based on the image information. The control unit B is electrically connected to the display unit A, the scanning signal and the image data signal are transmitted to each of the plurality of pixels based on the image information from the outside, and the pixel for each scanning line sequentially emits light by the scanning signal in accordance with the image data signal to scan the image, and the image information is displayed on the display unit A.

Figure 2:
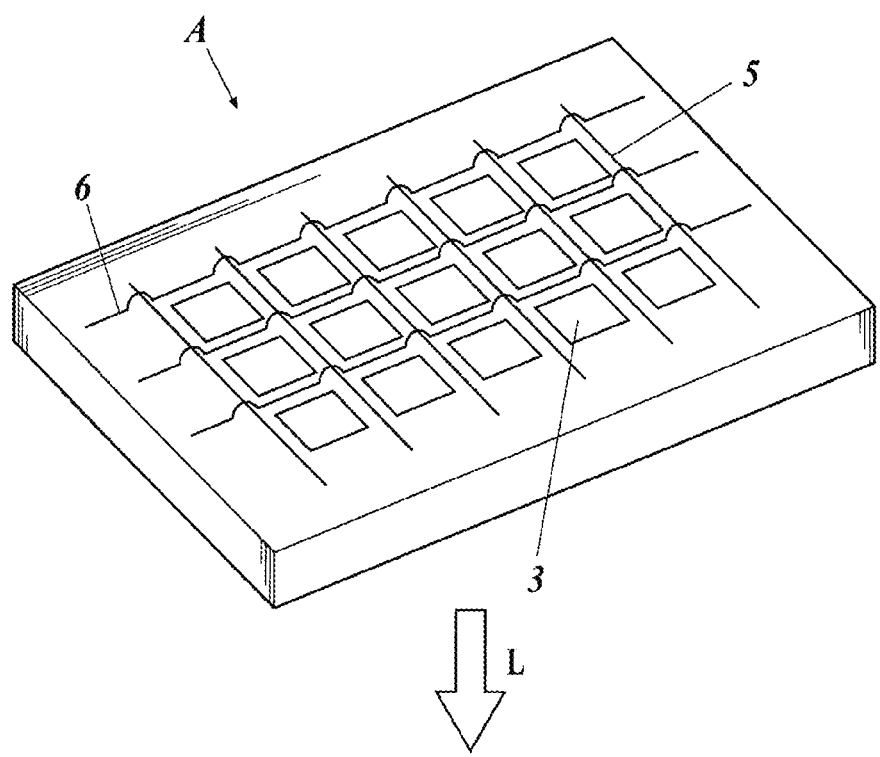
FIG. 2 is a schematic view of a display unit A in FIG. 1.

FIG. 2 is a schematic view of the display unit A.

The display unit A has a wiring section including a plurality of scanning lines 5 and data lines 6, a plurality of pixels 3, and the like on the substrate. The major members of the display unit A will be described below.

In FIG. 2, a case is illustrated in which light L emitted from the pixels 3 is extracted in the white arrow direction (downward direction).

Each of the scanning lines 5 and the plurality of data lines 6 in the wiring section is composed of a conductive material, and the scanning lines 5 and the data lines 6 cross each other at right angles and connected to the pixels 3 at the crossing positions (details are not illustrated).

The pixels 3 receive the image data signal from the data lines 6 and emit light in accordance with the received image data when the scanning signal is applied from the scanning lines 5. The full-color display in which the luminous color is full color is possible as the pixels in the red region, the pixels in the green region, and the pixels in the blue region are appropriately disposed on the same substrate side by side.

Figure 3:
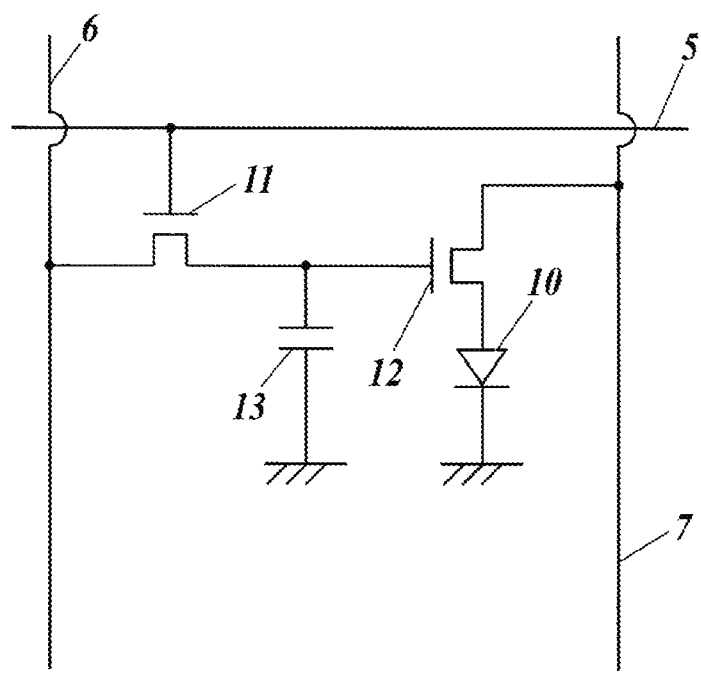
FIG. 3 is a circuit view of a pixel.

Next, the luminescence process of pixel will be described. FIG. 3 is a circuit view of a pixel. The pixel includes an organic EL element 10, a switching transistor 11, a driving transistor 12, a capacitor 13, and the like. It is possible to perform full-color display by using organic EL elements which emit light in red, green, and blue as the organic EL element 10 in a plurality of pixels and disposing these pixels on the same substrate side by side.

In FIG. 3, the image data signal is applied from the control unit B to the drain of the switching transistor 11 via the data line 6. Thereafter, the driving of the switching transistor 11 is turned on and the image data signal applied to the drain is transmitted to the capacitor 13 and the gate of the driving transistor 12 when the scanning signal is applied from the control unit B to the gate of the switching transistor 11 via the scanning line 5.

The driving of the driving transistor 12 is turned on as well as the capacitor 13 is charged in accordance with the potential of the image data signal by the transmission of the image data signal. In the driving transistor 12, the drain is connected to a power supply line 7, the source is connected to the electrode of the organic EL element 10, and an electric current is supplied from the power supply line 7 to the organic EL element 10 in accordance with the potential of the image data signal applied to the gate.

The driving of the switching transistor 11 is turned off when the scanning signal moves to the next scanning line 5 by sequential scanning by the control unit B. However, the capacitor 13 holds the charged potential of the image data signal although the driving of the switching transistor 11 is turned off, and thus the driving of the driving transistor 12 is maintained in an on state and the luminescence from the organic EL element 10 continues until the next scanning signal is applied. The driving transistor 12 is driven in accordance with the potential of the next image data signal synchronized with the scanning signal and the organic EL element 10 emits light when the next scanning signal is applied by sequential scanning.

In other words, with regard to the luminescence from the organic EL element 10, the luminescence from the respective organic EL elements 10 of a plurality of pixels 3 are performed by providing the switching transistor 11 and the driving transistor 12 which are an active element to the respective organic EL elements 10 of the plurality of pixels. Such a luminescence method is called an active matrix system.

Here, the luminescence from the organic EL element 10 may be the luminescence of a plurality of gradations by the multivalued image data signal having a plurality of gradation potentials or on and off of a predetermined amount of luminescence by the binary image data signal. In addition, the potential of the capacitor 13 may be continuously held until the next scanning signal is applied or it may be discharged immediately before the next scanning signal is applied.

In the present invention, the luminescence from the organic EL element is not limited to the active matrix system described above, but it may be luminescence driving by a passive matrix system in which the organic EL element emits light in accordance with the data signal only when the scanning signal is scanned.

Figure 4:
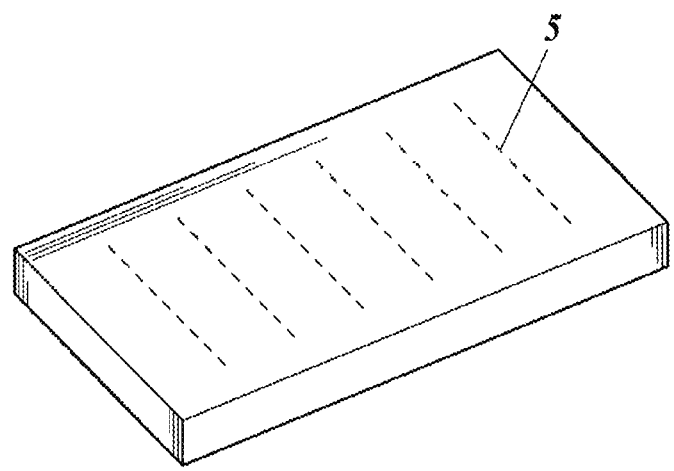
FIG. 4 is a schematic view of a passive matrix system full-color display device.
Figure 4:
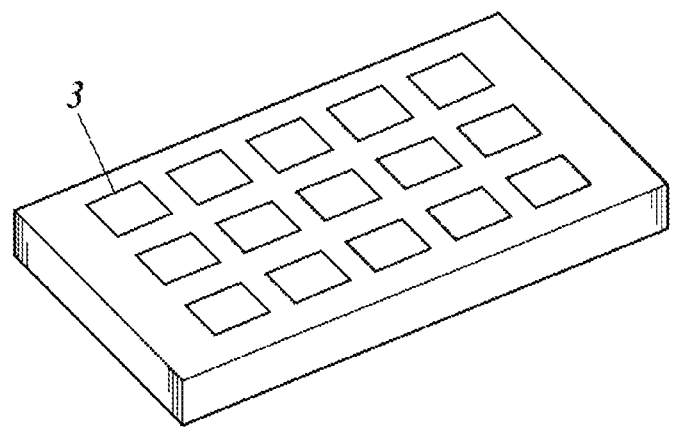
Figure 4:
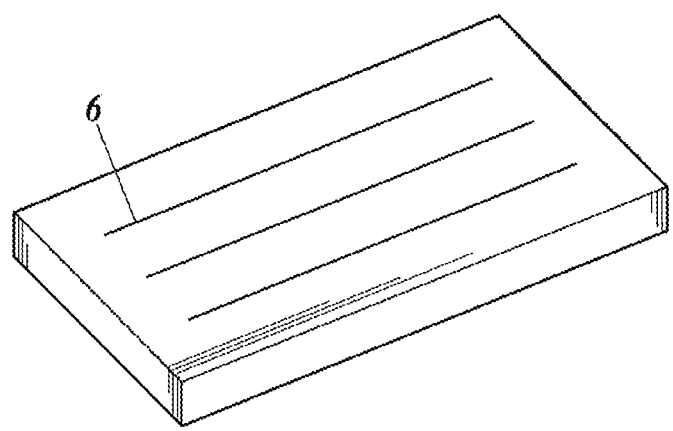

FIG. 4 is a schematic view of a display device by a passive matrix system. In FIG. 4, a plurality of scanning lines 5 and a plurality of image data lines 6 are provided in a lattice shape to face each other by sandwiching the pixel 3. The pixel 3 connected to the scanning line 5 emits light in accordance with the image data signal when the scanning signal of the scanning line 5 is applied to the pixel 3 by sequential scanning. In the passive matrix system, the pixel 3 does not include an active element and thus a decrease in manufacturing cost is achieved.

<<Lighting Device>>

The lighting device of the present invention will be described. The lighting device of the present invention is one that includes the organic EL element of the present invention. It may be used as an organic EL element obtained by having a resonator structure to the organic EL element of the present invention, and examples of the intended use of such an organic EL element having a resonator structure may include a light source for an optical storage medium, a light source for an electrophotographic copying machine, a light source for an optical communication processing machine, and a light source for an optical sensor, but it is not limited thereto. In addition, it may be used in the above applications after being subjected to the laser oscillation.

In addition, the organic EL element of the present invention may be used as a kind of lamp such as a light source for lighting or exposure, or it may be used as a projection device of a type to project an image or a display device (display) of a type to directly view a still image or a moving image. The driving system in the case of being used as a display device for reproducing a moving image may be either of a simple matrix (passive matrix) system or an active matrix system. Alternatively, it is possible to fabricate a full-color display device by using two or more kinds of the organic EL elements of the present invention having different luminous colors.

In addition, the organic EL material of the present invention can be applied to an organic EL element which emits light in substantially white as a lighting device. Light having a plurality of luminous colors is emitted at the same time from a plurality of luminescent materials so as to emit light in white by color mixing. The combination of a plurality of luminous colors may be one that contains three maximum luminescent wavelengths of the three primary colors of red, green, and blue or one that contains two maximum luminescent wavelengths utilizing the complementary color relation between blue and yellow, blue green and red.

In addition, the combination of the luminescent materials for obtaining a plurality of luminous colors may be either of the combination of a plurality of materials which emit light in a plurality of phosphorescence or fluorescence or the combination of a luminescent material which emits light in fluorescence or phosphorescence with a coloring material which emits the light from the luminescent material as excitation light, but in the organic EL element according to the present invention which emits light in white, it is only desirable to combine a luminescent dopant in addition to the phosphorescent organometallic complex according to the present invention and to mix them together.

The mask is provided only at the time of forming the luminous layer, the hole transport layer, the electron transport layer, or the like, the layer may be simply disposed so as to coat and separate using the mask, the other layers are common, thus the patterning of the mask or the like is not required, for example, an electrode film can be formed on the entire surface by a vapor deposition method, a casting method, a spin coating method, an ink-jet method, a printing method, and the like, and the productivity is also improved. According to this method, the element itself emits light in white unlike an organic EL device that is obtained by disposing elements emitting light in a plurality of colors parallel in an array shape and emits light in white. The luminescent material used for the luminous layer is not particularly limited, and for example, in the case of the backlight for a liquid crystal display device, a white color may be obtained by combining the metal complex according to the present invention with an arbitrary one selected from the known luminescent materials so as to fall in a wavelength range corresponding to the CF (color filter) characteristics.

<<One Aspect of Lighting Device of Present Invention>>

An aspect of the lighting device of the present invention that includes the organic EL element of the present invention will be described.

Figure 5:
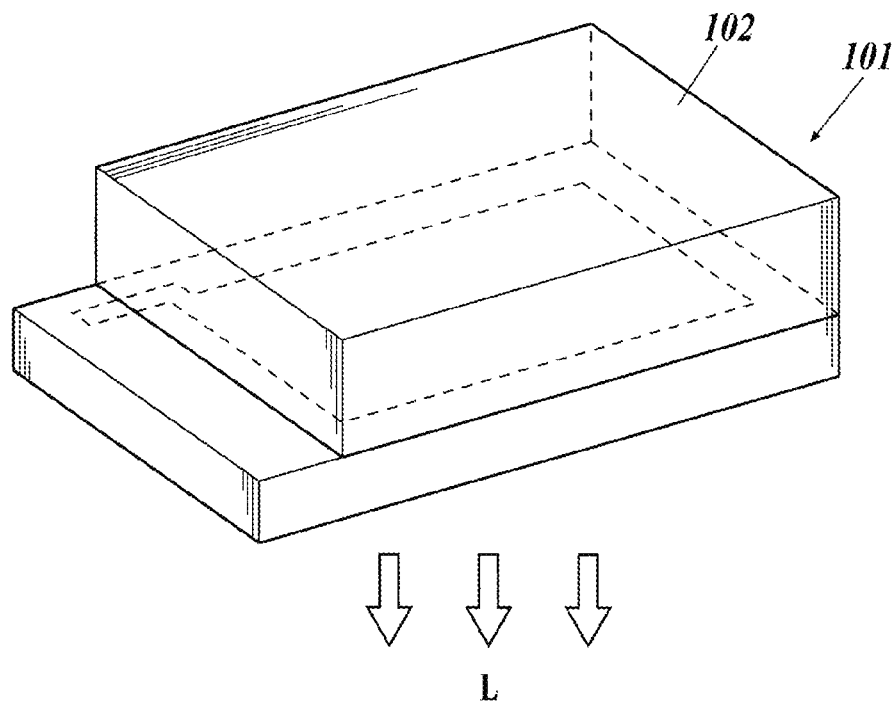
FIG. 5 is an outline view of a lighting device.
Figure 6:
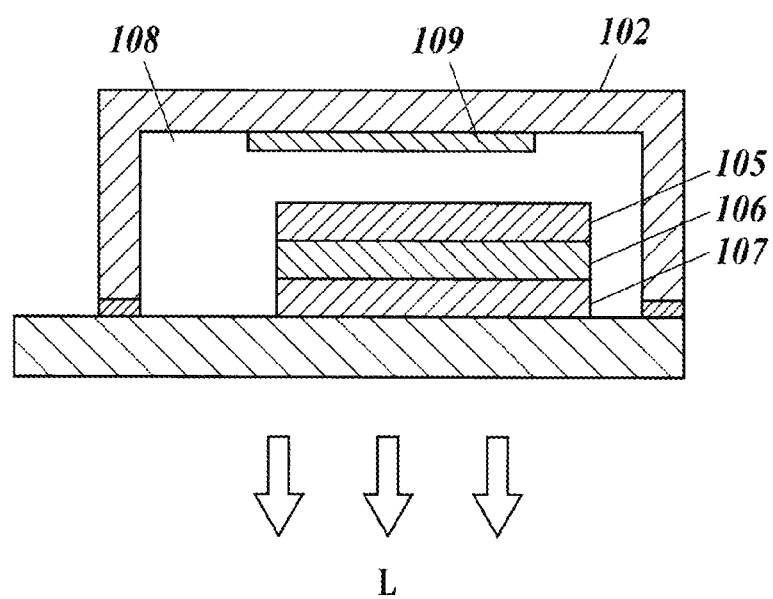
FIG. 6 is a schematic view of a lighting device.

The nonluminescent surface of the organic EL element of the present invention is covered with a glass cover, an epoxy-based photocurable adhesive (LUXTRACK LC0629B manufactured by TOAGOSEI CO., LTD.) as a sealing material is applied on the circumference of a glass substrate used as a substrate for sealing, this is superimposed on the negative electrode and brought into close contact with the transparent substrate, the epoxy-based photocurable adhesive is cured by being irradiated with UV light from the glass substrate side to seal the organic EL element, whereby it is possible to form the lighting device as illustrated in FIG. 5 and FIG. 6.

FIG. 5 illustrates a schematic view of a lighting device, and an organic EL element 101 of the present invention is covered with a glass cover 102 (incidentally, the sealing operation using the glass cover was conducted in a glove box in a nitrogen atmosphere (in an atmosphere of highly pure nitrogen gas having a purity of 99.999% or higher) without allowing the organic EL element 101 to contact with the air).

FIG. 6 illustrates a cross-sectional view of a lighting device, and in FIG. 6, reference numeral 105 denotes a negative electrode, reference numeral 106 denotes an organic EL layer, and reference numeral 107 denotes a glass substrate with transparent electrode. Incidentally, in the glass cover 102, a nitrogen gas 108 is filled and a water trapping agent 109 is provided.

EXAMPLES

Hereinafter, the present invention will be specifically described with reference to Examples, but the present invention is not limited thereto. Incidentally, the term "parts" or "%" used in Examples indicates the term "parts by mass" or "% by mass" unless otherwise stated.

Example 1

Fabrication of Organic EL Element 1-1

A substrate (NA45 manufactured by NH Techno Glass Corporation) was obtained by forming a film of ITO (indium tin oxide) as the positive electrode on a glass substrate of 100 mm×100 mm×1.1 mm in a thickness of 100 nm, this transparent substrate provided with an ITO transparent electrode was subjected to the ultrasonic cleaning with isopropyl alcohol, dried with a dry nitrogen gas, and subjected to the UV ozone cleaning for 5 minutes.

A thin film was formed on this transparent substrate using a solution of poly(3, 4-ethylenedioxythiophene)-polystyrene sulfonate (PEDOT/PSS CLEVIO P VP AI4083 manufactured by H.C. Starck GmbH) diluted to 70% with pure water by a spin coating method under the conditions of 3000 rpm and 30 seconds and then dried for 1 hour at 200° C., thereby providing a first hole transport layer having a thickness of 20 nm.

This transparent substrate was fixed to the substrate holder of a commercially available vacuum deposition apparatus, meanwhile, α-NPD as a hole transporting material was put in a molybdenum resistance heating boat by 200 mg, H-1 as a host compound was put in a separate molybdenum resistance heating boat by 200 mg, ET-8 as an electron transporting material was put in a separate molybdenum resistance heating boat by 200 mg, Comparative Compound 1 as a luminescent dopant was put in a separate molybdenum resistance heating boat by 100 mg, and these were attached to the vacuum deposition apparatus. The structural formula of each compound used will be presented later.

Subsequently, the pressure in the vacuum tank was reduced to $4 \times 10^{-4}$ Pa, the heating boat containing α-NPD was heated by applying an electric current thereto, and a second hole transport layer having a thickness of 20 nm was provided on the first hole transport layer at 0.1 nm/sec.

Furthermore, the heating boats containing H-1 as a host compound and Comparative Compound 1 as a luminescent dopant were heated by applying an electric current thereto, and H-1 and Comparative Compound 1 were co-deposited on the second hole transport layer at a deposition rate of 0.1 nm/sec and 0.025 nm/sec, respectively, thereby providing a luminous layer having a thickness of 30 nm.

Furthermore, the heating boat containing ET-8 was heated by applying an electric current thereto, and ET-8 was deposited on the luminous layer at a deposition rate of 0.1 nm/sec, thereby providing an electron transport layer having a thickness of 30 nm. Incidentally, the temperature of the substrate at the time of the deposition was room temperature.

Subsequently, lithium fluoride was deposited thereon to form a negative electrode buffer layer having a thickness of 0.5 nm, further aluminum was deposited thereon to forma negative electrode having a thickness of 110 nm, thereby fabricating the organic EL element 1-1 for Comparison.

Fabrication of Organic EL Elements 1-2 to 1-26

The organic EL elements 1-2 to 1-26 were fabricated by the same method as in the fabrication of the organic EL element 1-1 except that the luminescent dopant in the luminous layer was changed to the compounds described in Table 1.

Incidentally, the structures of the compounds used in Examples other than the compounds according to the present invention are presented below.

[Chemical Formula 20]

H-1

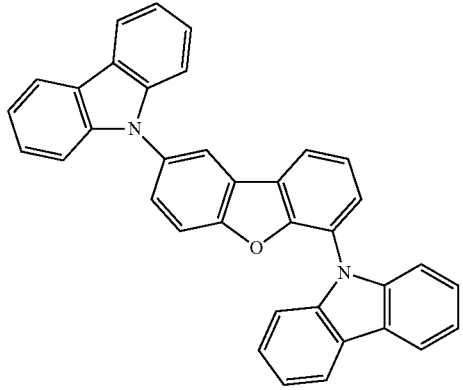

α-NPD

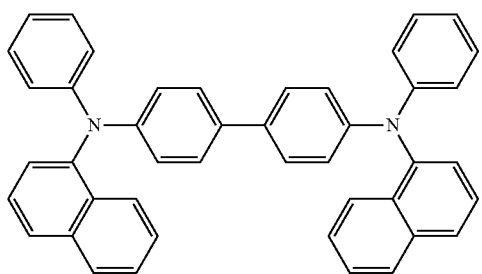

ET-β(BAlq)

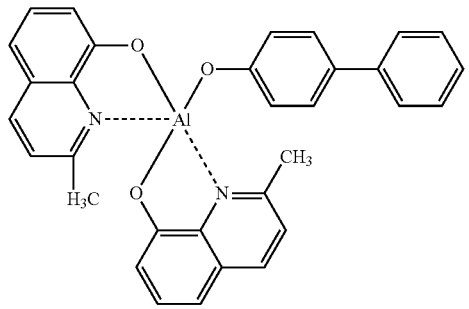

Comparative Compound 1

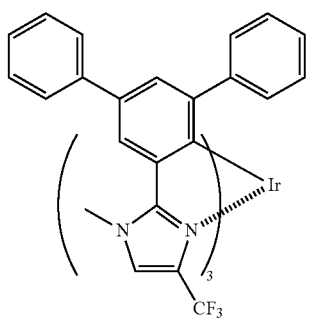

Comparative Compound 2

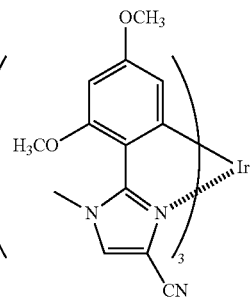

Comparative Compound 3

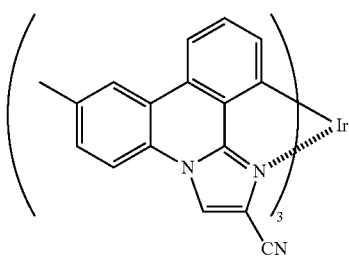

Evaluation of Organic EL Elements 1-1 to 1-26

Upon the evaluation of the organic EL elements 1-1 to 1-26, the evaluation was conducted for lighting devices as illustrated in FIG. 5 and FIG. 6 that were fabricated as follows using the organic EL elements 1-1 to 1-26. The nonluminescent surface of each of the organic EL elements thus fabricated was covered with a glass case, an epoxy-based photocurable adhesive (LUXTRACK LC0629B manufactured by TOAGOSEI CO., LTD.) as a sealing material was applied on the circumference of a glass substrate having a thickness of 300 μm as a substrate for sealing, this was superimposed on the negative electrode and brought into close contact with the transparent substrate, the epoxy-based photocurable adhesive was cured by being irradiated with UV light from the glass substrate side to seal the organic EL element.

For each sample fabricated in this manner, (1) lifespan, (2) driving voltage, (3) time-dependent change in driving voltage, and (4) change in external extraction quantum efficiency at high temperature were evaluated.

(1) Lifespan

The half-life was evaluated according to the following measurement method, and this was used as a measure of lifespan.

The organic EL element was subjected to constant current driving at an electric current to provide an initial brightness of 1000 cd/m$^2$ to the organic EL element at room temperature (25° C.), the time until the brightness reached ½ (500 cd/m$^2$) of the initial brightness was determined, and this was adopted as the half-life.

The half-life is presented in Table 1 as a relative value to 100 for the organic EL element 1-1. The lifespan is longer to be preferable as the value is greater.

(2) Driving Voltage

The voltage when the organic EL element was driven at room temperature (25° C.) under a constant current condition of 2.5 mA/cm$^2$ was measured for each organic EL element, and it is presented in Table 1 as a relative value to 100 for the organic EL element 1-1. The driving voltage is lower to be preferable as the value is smaller.

(3) Time-Dependent Change in Driving Voltage

The organic EL element was continuously lighted up at room temperature (25° C.) under a constant current condition of 2.5 mA/cm$^2$, and the driving voltage when the brightness reached 70% of the initial brightness was measured for each organic EL element. The measurement results are respectively presented in Table 1 as a relative value to 100 for the organic EL element 1-1 as expressed below. Incidentally, it indicates that the time-dependent change is smaller to be superior to Comparison as the value is smaller.

Change in driving voltage 1=(driving voltage of organic EL element 1-1 when having brightness of 70%)/(initial driving voltage of organic EL element 1-1)

Change in driving voltage of each element=(driving voltage of each element when having brightness of 70%)/(initial driving voltage of each element)

Time-dependent change in driving voltage=100×(change in driving voltage of each element)/(change in driving voltage 1)

(4) Change in External Extraction Quantum Efficiency at High Temperature

The organic EL element was lighted up at room temperature (25° C.) under a constant current condition of 2.5 mA/cm$^2$, and the luminescent brightness (L1) [cd/m$^2$] was measured immediately after the start of lighting up to calculate the external extraction quantum efficiency ($\eta$1). Furthermore, the organic EL element was subjected to the same measurement at 50° C., and the external extraction quantum efficiency ($\eta$2) was calculated from the luminescent brightness (L2).

Subsequently, the change in external extraction quantum efficiency of each element at a high temperature was determined as follows.

Change in external extraction quantum efficiency of each element at high temperature=($\eta$2 of each organic EL element)/($\eta$1 of each organic EL element)

Here, the measurement of the luminescent brightness was conducted using the CS-1000 (manufactured by Konica Minolta, Inc.), and the change in external extraction quantum efficiency at a high temperature was presented in Table 1 as a relative value to 100 for the organic EL element 1-1. It indicates that it is superior to Comparison as the value is greater.

TABLE 1

| Organic EL element | Luminescent dopant | Lifespan (relative value) | Driving voltage (relative value) | Time-dependent change in driving voltage (relative value) | Change in external extraction quantum efficiency at high temperature (relative value) | Remarks |
|---|---|---|---|---|---|---|
| 1-1 | Comparative Compound 1 | 100 | 100 | 100 | 100 | Comparative Example |
| 1-2 | Comparative Compound 2 | 103 | 110 | 115 | 95 | Comparative Example |
| 1-3 | Comparative Compound 3 | 105 | 100 | 120 | 110 | Comparative Example |
| 1-4 | Compound 1 | 220 | 70 | 68 | 132 | Present invention |
| 1-5 | Compound 2 | 218 | 70 | 70 | 130 | Present invention |
| 1-6 | Compound 4 | 215 | 70 | 70 | 128 | Present invention |
| 1-7 | Compound 5 | 210 | 73 | 72 | 125 | Present invention |
| 1-8 | Compound 9 | 210 | 73 | 72 | 125 | Present invention |
| 1-9 | Compound 14 | 190 | 72 | 72 | 118 | Present invention |
| 1-10 | Compound 16 | 190 | 79 | 77 | 120 | Present invention |
| 1-11 | Compound 17 | 195 | 79 | 77 | 120 | Present invention |
| 1-12 | Compound 18 | 187 | 77 | 78 | 120 | Present invention |
| 1-13 | Compound 19 | 222 | 69 | 67 | 132 | Present invention |
| 1-14 | Compound 20 | 160 | 83 | 83 | 112 | Present invention |
| 1-15 | Compound 21 | 170 | 80 | 80 | 115 | Present invention |
| 1-16 | Compound 24 | 160 | 83 | 83 | 110 | Present invention |
| 1-17 | Compound 26 | 165 | 85 | 85 | 112 | Present invention |
| 1-18 | Compound 27 | 165 | 85 | 85 | 112 | Present invention |
| 1-19 | Compound 28 | 208 | 74 | 75 | 123 | Present invention |
| 1-20 | Compound 29 | 175 | 78 | 78 | 117 | Present invention |
| 1-21 | Compound 30 | 205 | 74 | 75 | 123 | Present invention |
| 1-22 | Compound 73 | 173 | 80 | 78 | 115 | Present invention |
| 1-23 | Compound 102 | 205 | 73 | 74 | 125 | Present invention |
| 1-24 | Compound 203 | 170 | 80 | 78 | 113 | Present invention |
| 1-25 | Compound 204 | 180 | 75 | 77 | 115 | Present invention |
| 1-26 | Compound 214 | 170 | 82 | 77 | 113 | Present invention |

From Table 1, it can be seen that the organic EL elements 1-4 to 1-26 of the present invention exhibit improved properties as an element as the luminous lifespan is longer, the driving voltage is lower, and the time-dependent change in driving voltage and the change in external extraction quantum efficiency at a high temperature are smaller than those of the organic EL elements 1-1 to 1-3 of Comparative Examples.

Example 2

Fabrication of Organic EL Elements 2-1 to 2-23

The organic EL elements 2-1 to 2-23 were fabricated by the same method as in Example 1 except that H-1 of the host compound was changed to H-2 and the luminescent dopant in the luminous layer was changed to the compounds described in Table 2 in the organic EL element 1-1 of Example 1. The organic EL elements 2-1 to 2-23 thus obtained were respectively subjected to the evaluation on (1) lifespan, (2) driving voltage, (3) time-dependent change in driving voltage, and (4) change in external extraction quantum efficiency at high temperature by the same method as in Example 1. The evaluation results were respectively expressed as a relative value to 100 for the organic EL element 2-1. The results are presented in Table 2.

In addition, the structures of the compounds used other than the compounds according to the present invention are presented below.

[Chemical Formula 21]

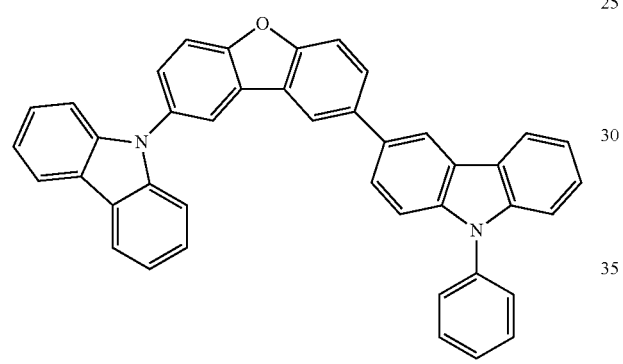

H-2

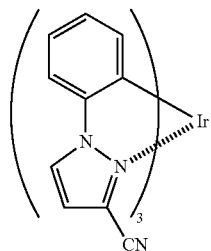

Comparative Compound 4

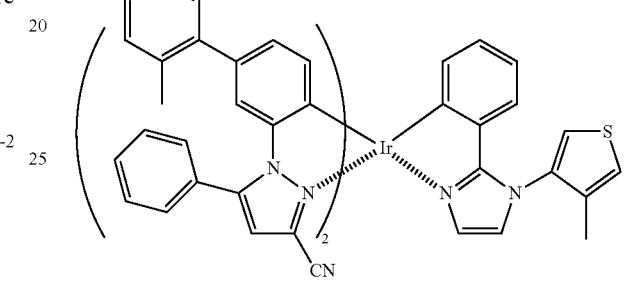

Comparative Compound 5

Comparative Compound 6

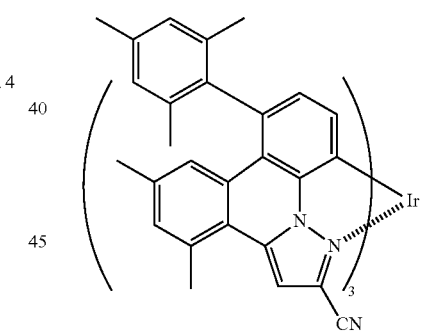

Comparative Compound 7

TABLE 2

| Organic EL element | Luminescent dopant | Lifespan (relative value) | Driving voltage (relative value) | Time-dependent change in driving voltage (relative value) | Change in external extraction quantum efficiency at high temperature (relative value) | Remarks |
|---|---|---|---|---|---|---|
| 2-1 | Comparative Compound 4 | 100 | 100 | 100 | 100 | Comparative Example |
| 2-2 | Comparative Compound 5 | 70 | 120 | 130 | 65 | Comparative Example |
| 2-3 | Comparative Compound 6 | 105 | 125 | 125 | 70 | Comparative Example |
| 2-4 | Comparative Compound 7 | 108 | 100 | 118 | 105 | Comparative Example |
| 2-5 | Compound 32 | 210 | 70 | 68 | 135 | Present invention |
| 2-6 | Compound 34 | 190 | 73 | 73 | 115 | Present invention |
| 2-7 | Compound 35 | 185 | 75 | 76 | 115 | Present invention |

TABLE 2-continued

| Organic EL element | Luminescent dopant | Lifespan (relative value) | Driving voltage (relative value) | Time-dependent change in driving voltage (relative value) | Change in external extraction quantum efficiency at high temperature (relative value) | Remarks |
|---|---|---|---|---|---|---|
| 2-8 | Compound 36 | 195 | 72 | 70 | 120 | Present invention |
| 2-9 | Compound 37 | 205 | 70 | 72 | 125 | Present invention |
| 2-10 | Compound 39 | 170 | 78 | 78 | 115 | Present invention |
| 2-11 | Compound 42 | 195 | 75 | 75 | 120 | Present invention |
| 2-13 | Compound 46 | 215 | 70 | 65 | 133 | Present invention |
| 2-14 | Compound 60 | 205 | 72 | 70 | 129 | Present invention |
| 2-15 | Compound 62 | 195 | 77 | 78 | 123 | Present invention |
| 2-16 | Compound 64 | 205 | 75 | 75 | 125 | Present invention |
| 2-17 | Compound 68 | 200 | 75 | 73 | 125 | Present invention |
| 2-18 | Compound 71 | 193 | 75 | 71 | 118 | Present invention |
| 2-19 | Compound 74 | 190 | 78 | 75 | 120 | Present invention |
| 2-20 | Compound 83 | 200 | 75 | 73 | 125 | Present invention |
| 2-21 | Compound 111 | 185 | 77 | 81 | 118 | Present invention |
| 2-22 | Compound 205 | 180 | 75 | 77 | 115 | Present invention |
| 2-23 | Compound 207 | 175 | 73 | 77 | 113 | Present invention |
| 2-23 | Compound 209 | 168 | 80 | 81 | 115 | Present invention |

From Table 2, it can be seen that the organic EL elements 2-5 to 2-23 of the present invention exhibit improved properties as an element as the luminous lifespan is longer, the driving voltage is lower, and the time-dependent change in driving voltage and the change in external extraction quantum efficiency at a high temperature are smaller than those of the organic EL elements 2-1 to 2-4 of Comparative Examples.

Comparative Compound 5 has an electron withdrawing group in $Rb_4$, and thus the maximum luminescent wavelength was a longer wavelength as compared to a case in which a substituent was introduced into Rx.

Example 3

Fabrication of Organic EL Elements 3-1 to 3-11

The organic EL elements 3-1 to 3-11 were fabricated by the same method as in Example 1 except that ET-8 in the electron transport layer was changed to ET-9 and the luminescent dopant in the luminous layer was changed to the compounds described in Table 3 in the organic EL element 1-1 of Example 1.

The organic EL elements 3-1 to 3-11 thus obtained were respectively subjected to the evaluation on (1) lifespan, (2) driving voltage, (3) time-dependent change in driving voltage, and (4) change in external extraction quantum efficiency at high temperature by the same method as in Example 1. The evaluation results were respectively expressed as a relative value to 100 for the organic EL element 3-1. The results are presented in Table 3.

In addition, the structures of the compounds used other than the compounds according to the present invention are presented below.

[Chemical Formula 22]

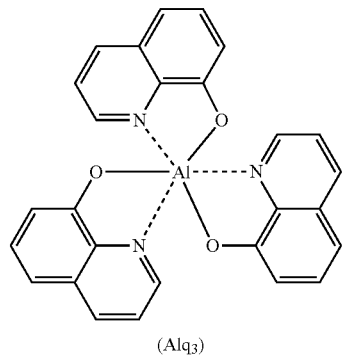

(Alq₃) ET-9

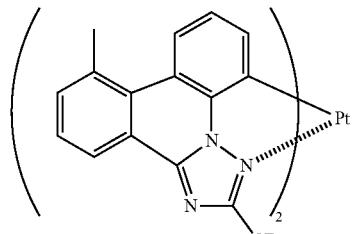

Comparative Compound 8

TABLE 3

| Organic EL element | Luminescent dopant | Lifespan (relative value) | Driving voltage (relative value) | Time-dependent change in driving voltage (relative value) | Change in external extraction quantum efficiency at high temperature (relative value) | Remarks |
|---|---|---|---|---|---|---|
| 3-1 | Comparative Compound 8 | 100 | 100 | 100 | 100 | Comparative Example |
| 3-2 | Compound 51 | 230 | 71 | 67 | 132 | Present invention |
| 3-3 | Compound 52 | 220 | 72 | 67 | 130 | Present invention |

TABLE 3-continued

| Organic EL element | Luminescent dopant | Lifespan (relative value) | Driving voltage (relative value) | Time-dependent change in driving voltage (relative value) | Change in external extraction quantum efficiency at high temperature (relative value) | Remarks |
|---|---|---|---|---|---|---|
| 3-4 | Compound 53 | 195 | 78 | 75 | 127 | Present invention |
| 3-5 | Compound 54 | 195 | 77 | 77 | 127 | Present invention |
| 3-6 | Compound 56 | 188 | 80 | 81 | 125 | Present invention |
| 3-7 | Compound 59 | 210 | 75 | 70 | 128 | Present invention |
| 3-8 | Compound 75 | 185 | 80 | 80 | 125 | Present invention |
| 3-9 | Compound 79 | 170 | 83 | 85 | 115 | Present invention |
| 3-10 | Compound 113 | 182 | 76 | 78 | 124 | Present invention |
| 3-11 | Compound 208 | 180 | 78 | 80 | 120 | Present invention |

From Table 3, it can be seen that the organic EL elements 3-2 to 3-11 of the present invention exhibit improved properties as an element as the luminous lifespan is longer, the driving voltage is lower, and the time-dependent change in driving voltage and the change in external extraction quantum efficiency at a high temperature are smaller than those of the organic EL element 3-1 of Comparative Example.

Example 4

Fabrication of Organic EL Element Emitting Light in White 4-1

A substrate (NA45 manufactured by NH Techno Glass Corporation) obtained by forming a film of ITO as the positive electrode on a glass substrate of 100 mm×100 mm×1.1 mm in 100 nm was patterned. Thereafter, this transparent substrate provided with an ITO transparent electrode was subjected to the ultrasonic cleaning with isopropyl alcohol, dried with a dry nitrogen gas, and subjected to the UV ozone cleaning for 5 minutes.

This transparent substrate was fixed to the substrate holder of a commercially available vacuum deposition apparatus, meanwhile, α-NPD as a hole transporting material was put in a molybdenum resistance heating boat by 200 mg, Host Compound H-1 as a host compound was put in a separate molybdenum resistance heating boat by 200 mg, ET-8 as an electron transporting material was put in a separate molybdenum resistance heating boat by 200 mg, Compound 1 (phosphorescent organometallic complex that emits light in blue) according to the present invention as a luminescent dopant was put in a separate molybdenum resistance heating boat by 100 mg, D-10 as a luminescent dopant was put in a separate molybdenum resistance heating boat by 100 mg, and these were attached to the vacuum deposition apparatus.

[Chemical Formula 23]

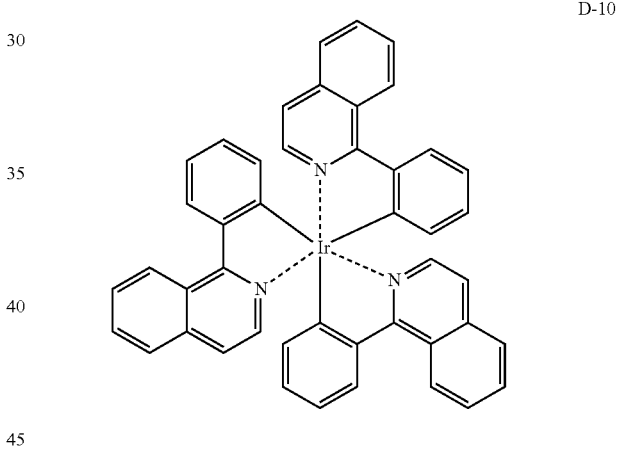

D-10

Subsequently, the pressure in the vacuum tank was reduced to $4\times10^{-4}$ Pa, an electric current was separately applied to each of the heating boats containing α-NPD, and α-NPD was deposited on the transparent substrate at a deposition rate of 0.1 nm/sec, thereby providing a hole transport layer having a thickness of 20 nm.

Furthermore, the heating boat containing Host Compound H-1 as a host compound, and the heating boat containing Compound 1 according to the present invention as a luminescent dopant, and the heating boat containing D-10 as a luminescent dopant were heated by applying an electric current thereto, and a luminous layer having a thickness of 30 nm was provided thereon by adjusting the deposition rate of the respective materials to 100:10:0.2.

Furthermore, the heating boat containing ET-8 was heated by applying an electric current thereto, and ET-8 was deposited on the luminous layer at a deposition rate of 0.1 nm/sec, thereby providing an electron transport layer having a thickness of 30 nm. Incidentally, the temperature of the substrate at the time of the deposition was room temperature.

Subsequently, lithium fluoride was deposited thereon to form a negative electrode buffer layer having a thickness of 0.5 nm, further aluminum was deposited thereon to form a negative electrode having a thickness of 110 nm, thereby fabricating the organic EL element 4-1.

Fabrication of organic EL elements 4-2 and 4-3

Organic EL Elements 4-2 and 4-3 were Fabricated in the same manner as in the fabrication of the organic EL element 4-1 except that the luminescent dopant used in the luminous layer was changed from Compound 1 according to the present invention to Compound 5 and Compound 9 according to the present invention in the fabrication of the organic EL element 4-1.

Evaluation of Organic EL Elements 4-1 to 4-3

An electric current was applied to the organic EL elements 4-1 to 4-3 thus fabricated and light in white was obtained, thus it has been found that the organic EL elements 4-1 to 4-3 thus fabricated can be used as a lighting device emitting light in white.

Example 5

Fabrication of Organic EL Element Emitting Light in White 5-1

FIGS. 7A to 7E illustrate schematic configuration views of an organic EL full-color display device. A substrate (NA45 manufactured by NH Techno Glass Corporation) obtained by forming a film of ITO transparent electrode 202 as the positive electrode on a glass substrate 201 in 100 nm was patterned at a pitch of 100 μm (see FIG. 7A), and a partition wall 203 (width: 20 μm, thickness: 2.0 μm) of a non-photosensitive polyimide was formed on this glass substrate 201 and between the ITO transparent electrodes 202 by photolithography (see FIG. 7B).

Figure 7A:
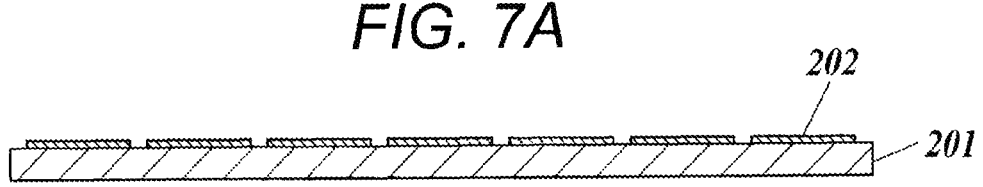
FIG. 7A is a schematic configuration view of an organic EL full-color display device.
Figure 7B:
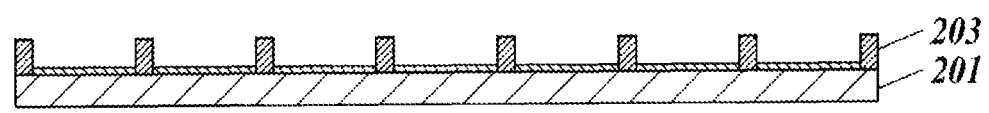
FIG. 7B is a schematic configuration view of an organic EL full-color display device.
Figure 7C:
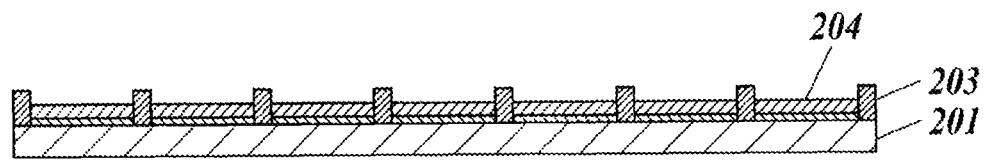
FIG. 7C is a schematic configuration view of an organic EL full-color display device.

A hole injection layer composition having the following composition was ejected and injected onto the ITO electrode 202 and between the partition walls 203 using an ink-jet head (MJ800C manufactured by SEIKO EPSON CORPORATION), irradiated with ultraviolet light for 200 seconds, and subjected to the drying treatment for 10 minutes at 60° C., thereby providing a hole injection layer 204 having a thickness of 40 nm (see FIG. 7C).

Figure 7D:
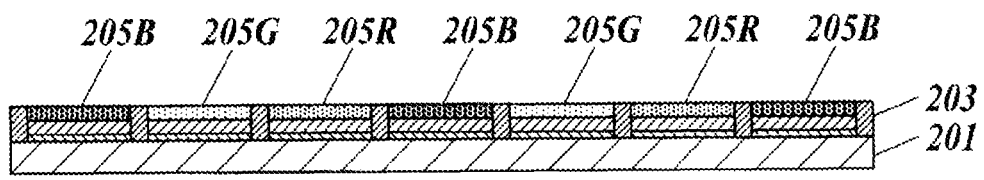
FIG. 7D is a schematic configuration view of an organic EL full-color display device.

A blue luminous layer composition, a green luminous layer composition, and a red luminous layer composition which respectively had the following compositions were ejected and injected on the hole injection layer 204 in the same manner using an ink-jet head and subjected to the drying treatment for 10 minutes at 60° C., thereby providing luminous layers 205B, 205G, and 205R exhibiting the respective colors (see FIG. 7D).

| (Hole injection layer composition) | |
| --- | --- |
| HT-1 | 20 parts by mass |
| Cyclohexylbenzene | 50 parts by mass |
| Isopropylbiphenyl | 50 parts by mass |
| (Blue luminous layer composition) | |
| Host compound H-3 | 0.70 part by mass |
| Compound 19 | 0.04 part by mass |
| Cyclohexylbenzene | 50 parts by mass |
| Isopropylbiphenyl | 50 parts by mass |

-continued

| (Green luminous layer composition) | |
| --- | --- |
| Host compound H-3 | 0.70 part by mass |
| D-1 | 0.04 part by mass |
| Cyclohexylbenzene | 50 parts by mass |
| Isopropylbiphenyl | 50 parts by mass |
| (Red luminous layer composition) | |
| Host compound H-3 | 0.70 part by mass |
| D-10 | 0.04 part by mass |
| Cyclohexylbenzene | 50 parts by mass |
| Isopropylbiphenyl | 50 parts by mass |

[Chemical Formula 24]

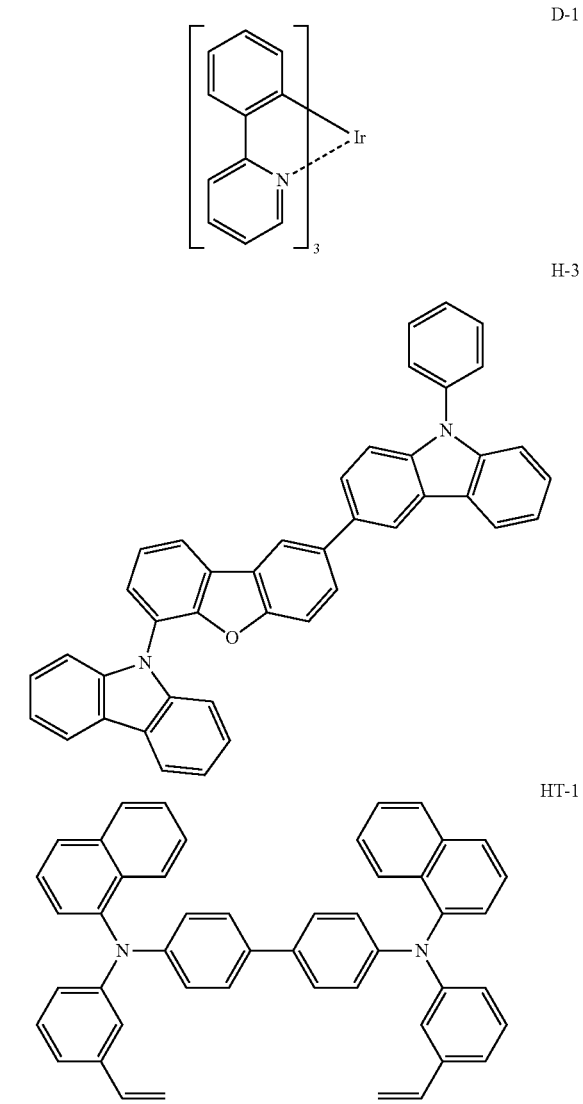

Figure 7E:
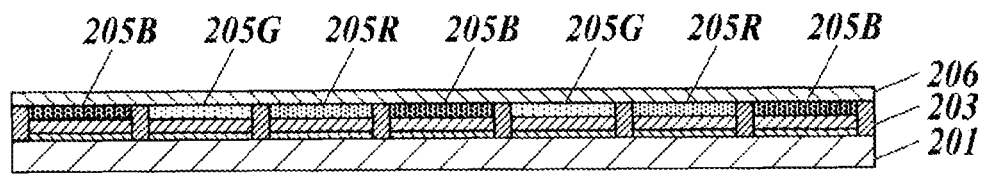
FIG. 7E is a schematic configuration view of an organic EL full-color display device.

Subsequently, an electron transport layer having a layer thickness of 20 nm (not illustrated) was provided by depositing ET-8 so as to cover the respective coloring layers 205B, 205G, and 205R, further, a negative electrode buffer layer having a layer thickness of 0.6 nm (not illustrated) was provided by depositing lithium fluoride thereon, and a negative electrode 206 having a layer thickness of 130 nm was provided by depositing aluminum thereon, thereby fabricating an organic EL element (see FIG. 7E).

The organic EL element thus fabricated exhibited colors of blue, green, and red as a voltage was applied to the respective electrodes, thus it has been found that the organic EL element thus fabricated can be utilized as a full-color display device.

INDUSTRIAL APPLICABILITY

The organic EL element of the present invention can be preferably applied to a lighting device and a display device as it has a shorter maximum luminescent wavelength, a long luminous lifespan, a low driving voltage, a small time-dependent change in driving voltage, and a small change in external extraction quantum efficiency even when being used at a high temperature.

REFERENCE SIGNS LIST

1 Display
3 Pixel
5 Scanning line
6 Data line
7 Power supply line
10 Organic EL element
11 Switching transistor
12 Driving transistor
13 Capacitor
A Display unit
B Control unit
101 Lighting device
102 Glass cover
105 Negative electrode
106 Organic EL layer
107 Glass substrate
108 Nitrogen gas
109 Water trapping agent
201 Glass substrate
202 ITO transparent electrode
203 Partition wall
204 Hole injection layer
205B, 205G, and 205R luminous layer
206 Negative electrode
L Light

The invention claimed is:

1. An organic electroluminescent element comprising:
at least one luminous layer sandwiched between a positive electrode and a negative electrode,
wherein the luminous layer contains at least one kind of phosphorescent organometallic complex having a structure represented by Formula (1):

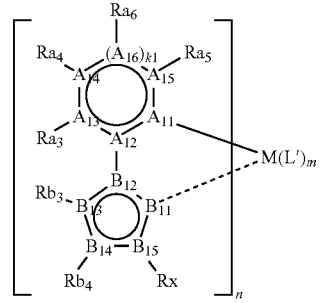

wherein $A_{11}$ to $A_{16}$ represents an aromatic hydrocarbon ring or an aromatic heterocyclic ring,
$B_{11}$ to $B_{15}$ represents an aromatic heterocyclic ring,
$A_{11}$ and $A_{12}$ each independently represent C or N,
$A_{13}$ to $A_{16}$ each independently represent any one of C, N, O, or S,
k1 represents an integer of 0 or 1, $A_{14}$ and $A_{15}$ are directly bonded to each other when k1 is 0,
Rx represents an electron withdrawing group and is a cyano group,
$Ra_3$, $Ra_4$, $Ra_5$, or $Ra_6$ is not present on O or S when any one of $A_{13}$ to $A_{16}$ is O or S,
$Ra_3$, $Ra_4$, $Ra_5$, or $Ra_6$ is optionally not present on N when any one of $A_{13}$ to $A_{16}$, is N,
$Ra_3$ to $Ra_6$ and $Rb_3$ to $Rb_4$ each represent a hydrogen atom or a substituent
$Rb_3$ and $Ra_3$ are not joined to form a ring,
M represents iridium or platinum,
L' represents a monoanionic bidentate ligand,
n represents an integer from 1 to 3, and m represents an integer from 0 to 2.

2. The organic electroluminescent element according to claim 1, wherein a substituent represented by $Ra_3$ in the phosphorescent organometallic complex represented by Formula (1) is a fluorine atom.

3. The organic electroluminescent element according to claim 1, comprising at least one luminescent dopant exhibiting a luminous color different from the luminous color of the phosphorescent organometallic complex in addition to the phosphorescent organometallic complex represented by Formula (1) and emitting light in white.

4. A lighting device comprising the organic electroluminescent element according to claim 1.

5. A display device comprising the organic electroluminescent element according to claim 1.

6. The organic electroluminescent element according to claim 1, wherein at least any one pair of two adjacent substituents among $Ra_3$ to $Ra_6$ are bonded to each other to form the ring structure.

7. The organic electroluminescent element according to claim 1, wherein the luminous layer further comprises a host compound having a carbazole ring and a dibenzofuran ring.

* * * * *